(12) United States Patent
Teraoka et al.

(10) Patent No.: US 9,222,835 B2
(45) Date of Patent: Dec. 29, 2015

(54) MULTI-ANGLE COLORIMETER

(71) Applicant: Konica Minolta, Inc., Tokyo (JP)

(72) Inventors: Yoshitaka Teraoka, Osaka (JP); Katsutoshi Tsurutani, Osaka (JP); Yuta Yamanoi, Toyonaka (JP)

(73) Assignee: Konica Minolta, Inc., Tokyo (JP)

( * ) Notice: Subject to any disclaimer, the term of this patent is extended or adjusted under 35 U.S.C. 154(b) by 0 days.

(21) Appl. No.: 14/660,543

(22) Filed: Mar. 17, 2015

(65) Prior Publication Data

US 2015/0192469 A1    Jul. 9, 2015

Related U.S. Application Data

(63) Continuation of application No. 14/114,464, filed as application No. PCT/JP2012/059364 on Apr. 5, 2012, now Pat. No. 9,001,329.

(30) Foreign Application Priority Data

Apr. 28, 2011    (JP) .................................. 2011-101742

(51) Int. Cl.
*G01J 3/46*    (2006.01)
*G01J 3/50*    (2006.01)
*G01J 3/08*    (2006.01)
(Continued)

(52) U.S. Cl.
CPC ................. *G01J 3/50* (2013.01); *G01J 3/0218* (2013.01); *G01J 3/0272* (2013.01); *G01J 3/08* (2013.01); *G01J 3/504* (2013.01); *G01N 21/251* (2013.01); *G01N 21/255* (2013.01); *G01N 2021/4711* (2013.01); *G01N 2021/4735* (2013.01); *G01N 2021/575* (2013.01); *G01N 2201/0221* (2013.01); *G01N 2201/061* (2013.01); *G01N 2201/08* (2013.01)

(58) Field of Classification Search
CPC ................. G01J 3/02; G01J 3/46; G01J 3/50; G01J 3/51; G01J 3/524
USPC .................................................. 356/402–425
See application file for complete search history.

(56) References Cited

U.S. PATENT DOCUMENTS 6,473,165 B1   10/2002  Coombs et al.
6,707,553 B1 *  3/2004  Imura ........................... 356/402
(Continued)

FOREIGN PATENT DOCUMENTS

JP    09-68462    3/1997
JP    9-068462    3/1997
(Continued)

*Primary Examiner* — Abdullahi Nur
(74) *Attorney, Agent, or Firm* — Cozen O'Connor

(57) ABSTRACT

A multi-angle colorimeter employs a multi-angle mode and a symmetrical arrangement mode in an optical arrangement. Light detection on both sides of the symmetrical arrangement is performed by a single photodetector unit. The photodetector unit is used on both sides, and thus, the device becomes simpler, without any impact on individual difference in characteristics of multiple photodetector units. Conversely, elements for illumination can be used on both sides. Also in a case where multiple photodetector units are used, the size and cost of the device can be reduced with the use of a photodetector unit having a relatively low wavelength resolution as a photodetector unit to be used on one side. This enables to reduce an attitude error due to relative tilting of a measurement surface while reducing the size and cost of the device.

4 Claims, 17 Drawing Sheets

(51) Int. Cl.
*G01J 3/02* (2006.01)
*G01N 21/25* (2006.01)
*G01N 21/47* (2006.01)
*G01N 21/57* (2006.01)

(56) References Cited

U.S. PATENT DOCUMENTS

| | | |
|---|---|---|
| 7,027,160 B2 | 4/2006 | Sperling |
| 7,483,133 B2 | 1/2009 | Bareket et al. |
| 7,719,687 B2 | 5/2010 | Matsumoto et al. |
| 8,634,069 B2 | 1/2014 | Nakano et al. |
| 2006/0215162 A1 | 9/2006 | Shannon et al. |

FOREIGN PATENT DOCUMENTS

| | | |
|---|---|---|
| JP | 2001-050817 | 2/2001 |
| JP | 2002-005830 | 1/2002 |
| JP | 2003-521040 | 7/2003 |
| JP | 2005-000987 | 1/2005 |
| JP | 2007-315761 | 12/2007 |
| JP | 2008-523392 | 7/2008 |
| JP | 2009-264924 | 11/2009 |
| WO | WO 01/54077 | 7/2001 |

\* cited by examiner

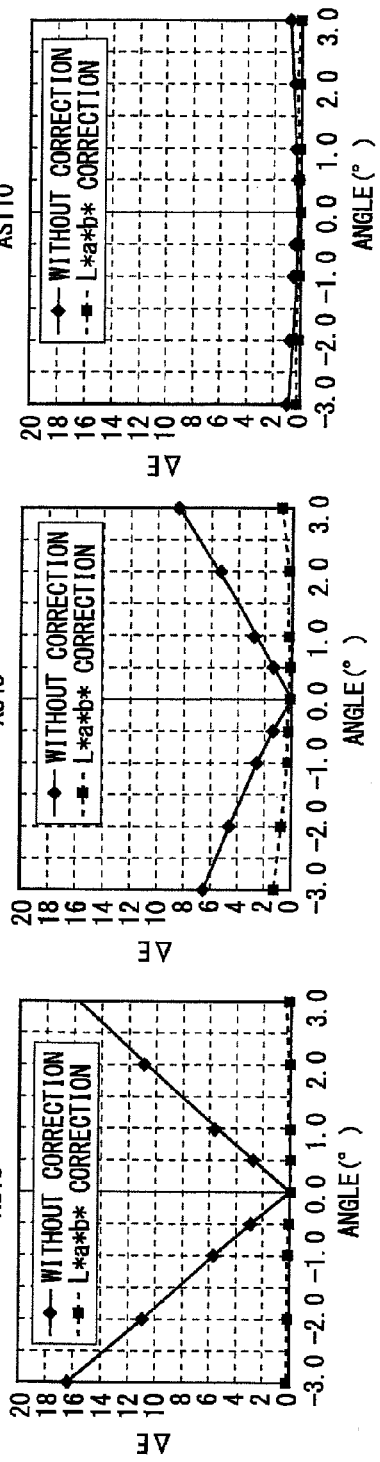
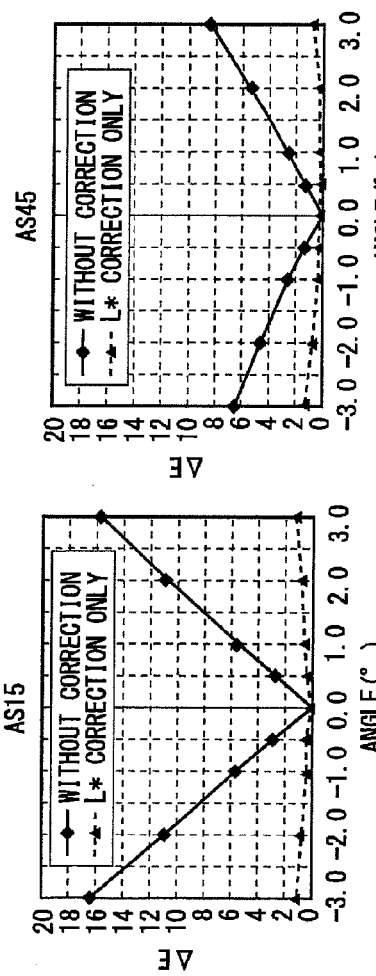
FIG. 14A  FIG. 14B  FIG. 14C  FIG. 14D  FIG. 14E  FIG. 14F

MULTI-ANGLE COLORIMETER

CROSS REFERENCE TO RELATED APPLICATIONS

This application is a continuation of U.S. patent application Ser. No. 14/114,464 which was filed with the U.S. Patent and Trademark Office on Oct. 28, 2013. Priority is claimed for this invention and application, which is a U.S. National Phase Application under 35 USC 371 of International Application PCT/JP2012/059364 filed Apr. 5, 2012. This application claims the priority of Japanese application No. 2011-101742 filed Apr. 28, 2011, the entire content of which are hereby incorporated by reference.

TECHNICAL FIELD

The present invention relates to a multi-angle colorimeter, and more particularly, to the technology of improving an optical arrangement for correcting an attitude error of a colorimeter with respect to a measurement surface.

BACKGROUND ART

Metallic coating, pearl color coating, and other coating for use in car coating may appear to vary in color depending on an observer's angle due to a radiant material of the interior. For this reason, a multi-angle colorimeter that performs illumination or light receiving at multiple angles is used for coating evaluation (evaluation of coating color).

In other words, in metallic coating and pearl color coating for use in car coating, coating films contain aluminum flakes and mica flakes referred to as radiant materials, which produce a so-called metallic effect and pearl effect. This is because the radiant material contributes to reflection characteristics differently depending on the directions of illumination and observation. A multi-angle colorimeter having a multi-angle geometry (optical arrangement) for illuminating a sample surface of an object to be measured from multiple directions and receiving the light from one direction (multi-directional illumination and unidirectional light receiving) or illuminating a sample surface of an object to be measured from one direction and receiving the lights from multiple directions (unidirectional illumination and multidirectional light receiving) is used in the evaluation (colorimetry) of metallic coating and pearl color coating.

Unfortunately, in a case where an object to be measured is a sample having a curvature, such as a car bumper, an attitude error is highly likely to occur, where a sample normal does not coincide with a reference axis of a colorimeter in measurement. Among others, an angular orientation close to the specularly reflected light has large angle dependence in the reflection characteristics, and thus, an effect of this error is not negligible.

In order to reduce the attitude error, for example, the method disclosed in Japanese Patent Application Laid-Open No. 2002-5830 proposes the technology in which an optical base unit containing a measurement optical system is held by an elastic body such as a spring against a housing, and the illumination and light receiving geometories are kept constant irrespective of the contact angle between the sample and the housing, to thereby reduce an attitude error.

An example of another well-known technology is the technology in which multiple contact pins are arranged on a sample contact surface such that a measurement is triggered if those pins are pressed evenly, to thereby suppress an attitude error of a colorimeter.

Meanwhile, the method disclosed in Japanese Patent Application Laid-Open No. 2007-315761 proposes the technique in which in a glossimeter that measures a gloss of a sample from the specularly reflected light, an optical system for correction is additionally arranged to be axisymmetric with the original illumination system and light receiving system about a sample normal for suppressing an attitude error of the glossimeter, to thereby average measured values of the both systems.

Patent Document 1: Japanese Patent Application Laid-Open No. 2002-5830
Patent Document 2: Japanese Patent Application Laid-Open No. 2007-315761

SUMMARY OF THE INVENTION

Problems to be Solved by the Invention

The technology of Japanese Patent Application Laid-Open No. 2002-5830 above aims to reduce an attitude error by adding a twist to a mechanism, which requires a structurally complex mechanical configuration such as holding of an internal mechanism by an elastic body, resulting in an increase in device size. The internal mechanism has a moving structure, and thus it is feared that the reliability and durability will become poor in a case where the device is used on stringent conditions such as a case where an object to be measured is moving in a car manufacturing line.

In the well-known technology above, a measurer needs to manually adjust an attitude of the device, and unfortunately, it requires time and effort to start a measurement.

While the drawbacks of the technology of Japanese Patent Application Laid-Open No. 2002-5830 and well-known technology are solved in the technology of Japanese Patent Application Laid-Open No. 2007-315761, two pairs of components are purely required for light receiving systems such as sensors and peripheral circuit systems. Accordingly, it is feared that the device will become more complex and costly.

The present invention has been made in view of the above-mentioned circumstances, and therefore has an object to provide a multi-angle colorimeter capable of preventing, regarding the occurrence of an error due to an attitude error, an increase in components caused by merely arranging multiple pairs of optical systems having the same configuration, to thereby correct the attitude error while reducing the device size and cost.

Means to Solve the Problems

A multi-angle colorimeter according to one aspect of the present invention includes (a) multiple first illumination sections that are arranged on a virtual reference plane including a predetermined reference line and perform light irradiation at different angles toward a predetermined measurement point defined on the reference line, (b) multiple second illumination sections that are respectively arranged symmetrically with the multiple first illumination sections about the reference line on the reference plane and perform light irradiation toward the predetermined measurement point, (c) a photodetector section including: first and second light receiving windows arranged on the reference plane, face the measurement point, and are arranged symmetrically about the reference line; and a single photodetector unit including a photoelectric conversion element that receives first and second lights respectively received through the first and second light receiving windows and converts the received lights into electric signals, and (d) a computing section that determines detection values of the first and second lights based on the signals and obtains color information of a measurement surface located at the measurement point based on the detection values.

A multi-angle colorimeter according to another aspect of the present invention includes (a) multiple first illumination sections that are arranged on a virtual reference plane including a predetermined reference line and perform light irradiation at different angles toward a predetermined measurement point defined on the reference line, (b) multiple second illumination sections that are respectively arranged symmetrically with the multiple first illumination sections about the reference line on the reference plane and perform light irradiation toward the predetermined measurement point, (c) a photodetector section including: first and second light receiving windows arranged on the reference plane, face the measurement point, and are arranged symmetrically about the reference line; a first photodetector unit including a first photoelectric conversion element that receives a first light received through the first light receiving window and converts the first light into an electric signal; and a second photodetector unit including a second photoelectric conversion element that receives a second light received through the second light receiving window and converts the second light into an electric signal, and (d) a computing section that determines detection values of the first and second lights based on the signals and obtains color information of a measurement surface located at the measurement point based on the detection values, wherein a photodetector unit having a lower wavelength resolution than that of the first photodetector unit is used as the second photodetector unit.

A multi-angle colorimeter according to still another aspect of the present invention includes (a) a first illumination section that is arranged on a virtual reference plane including a predetermined reference line and performs light irradiation at a predetermined angle toward a predetermined measurement point defined on the reference line, (b) a second illumination section that is arranged symmetrically with the first illumination section about the reference line on the reference plane and performs light irradiation toward the measurement point, (c) a photodetector section including multiple pairs of photoelectric conversion elements that are arranged symmetrically about the reference line on the reference plane, each of the multiple pairs facing the measurement point, and (d) a computing section that obtains color information of a measurement surface located at the measurement point based on detection values respectively obtained from photoelectric conversion signals of the multiple pairs of photoelectric conversion elements, wherein the first illumination section and the second illumination section share a light source.

Effects of the Invention

According to the configuration described above, the color is measured based on the information of the reflected lights obtained in a symmetrical optical arrangement, whereby the color can be measured appropriately even if the reference line is tilted from the normal of the sample surface in the reference plane. In addition, the size and cost can be reduced by employing, for example, the configuration in which a single photodetector unit detects the first and second lights received through the first and second light receiving windows, the configuration in which a light source is shared between the first illumination section and second illumination section, or the configuration in which a photodetector unit having a lower wavelength resolution than that of the first photodetector unit is used as the second photodetector unit. Further, a single photodetector unit is used in common, and thus, internal parts thereof can be used in common. This eliminates the need to take into account an individual difference between detection units occurring in a case where multiple photodetector units are used. Further, a light source is used in common, which eliminates the need to take into account an individual difference between light sources occurring in a case where multiple light sources are used.

BRIEF DESCRIPTION OF DRAWINGS

FIGS. 14A to 14F shows graphs indicating measured values based on an experiment of correcting an attitude error through a symmetrical arrangement.

EMBODIMENTS FOR CARRYING OUT THE INVENTION

<1. Overview of Embodiments>
<1-1. External Appearance and Use Mode>

Figure 1A:
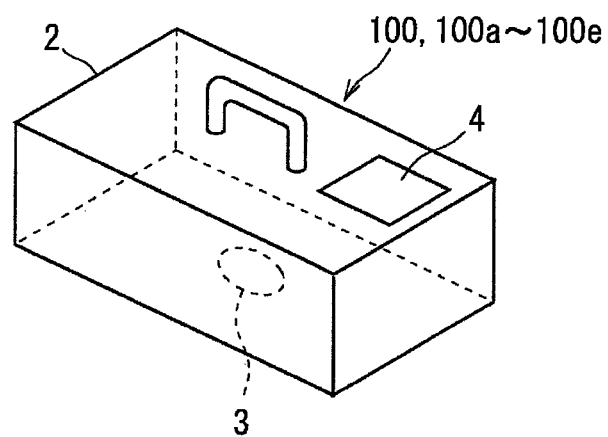
FIG. 1A is a perspective view showing an external appearance of a multi-angle colorimeter according to embodiments of the present invention.
Figure 1B:
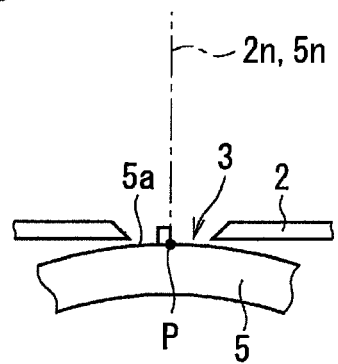
FIG. 1B is a schematic view describing an angular relationship between a central axis of a measuring device body and a measurement surface of a measurement sample thereof.

FIGS. 1A and 1B show a perspective view showing an external appearance common to multi-angle colorimeters according to embodiments of the present invention and a schematic view describing a positional relationship between a measuring device body and a measurement surface of an object to be measured.

FIG. 1A is the perspective view showing the external appearance of the multi-angle colorimeter. As shown in FIG. 1A, a multi-angle colorimeter 100 (100a to 100e) is formed of a box-shaped measuring device body 2 containing components (see FIGS. 7, 9, 10, 13, 16A, 16B and 18) described below. The measuring device body 2 comprises a measurement opening 3 drilled into a bottom wall and an operation display panel 4 that is disposed at an appropriate location on the surface and includes a display showing measurement results, an operational switch, and the like. The measuring device body 2 forms a portable colorimeter that can be carried.

FIG. 1B is the schematic view describing an angle between a central axis of the measuring device body of the multi-angle colorimeter and a measurement surface of a measurement sample. As shown in FIG. 1B, a measurement is performed with the measurement opening 3 of the multi-angle colorimeter 100 (100a to 100e) being directed to an object to be measured 5, where an area of the object to be measured 5 that faces the measurement opening 3 is a measurement area 5a. In measurement, the measuring device body 2 is arranged to face the surface of the object to be measured 5 such that a central axis 2n of the measuring device body 2 (normal of the measurement opening 3) coincides with a normal 5n of the measurement area 5a.

In a case where the object to be measured 5 has a curved surface, such as a vehicle bumper, it is difficult to cause the central axis 2n of the measuring device body 2 to accurately coincide with the normal 5n of the measurement surface. For this reason, the central axis 2n normally does not coincide with the normal of the measurement surface in many cases and is tilted with respect to the normal of the measurement surface. The above-mentioned measurement environment is referred to as "tilt environment" below.

<1-2. Meaning of Symmetrical Arrangement in Tilt Environment>

In each of the embodiments described below, a multi-angle colorimeter includes multiple light-receiving elements arranged correspondingly to one illumination element and is of a symmetrical arrangement mode in which pairs of the light-receiving elements are combined axisymmetrically.

Of those, the multi-angle mode is advantageous in that the reflected light obtained by the reflection of the light from one illumination element on a measurement surface is received at different angles to enhance a function of detecting the reflected light. The advantage of the symmetrical arrangement mode is as described below, where one illumination and one light receiving mode is taken as a simple model in which pairing is made axisymmetrically for paying attention to the symmetrical arrangement mode. The conditions below are also similar in the multi-angle mode.

FIGS. 2 to 5 are views and diagrams describing the circumstances caused by a deviation in angle between the central axis of the measuring device body and the measurement surface of the object to be measured. It is to be noted that the angle to be formed from the normal 5n toward the right of the sheet is defined as positive and the angle to be formed from the normal 5n toward the left of the sheet is defined as negative.

Figure 2:
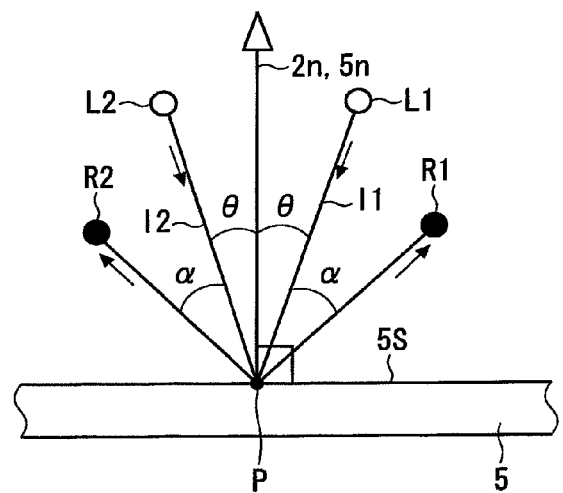
FIG. 2 is a view showing a positional relationship between an optical system and a measurement surface.

FIG. 2 is a view showing the positional relationship between the optical system and measurement surface in a case where the central axis 2n of the measuring device body 2 coincides with the normal 5n of a measurement surface 5s. As shown in FIG. 2, in a case where an illumination light 11 is radiated from an illumination system L1 located in a direction tilted from the normal 5n by an angle +θ, the illumination light 11 is reflected at a measurement point P of the measurement surface 5s and is received by a light receiving system R1 located in a direction tilted from the normal 5n by an angle +(θ+α) or a light receiving system R2 located in a direction tilted from the normal 5n by an angle −(θ+α). Similarly in a case where an illumination light 12 is radiated from an illumination system L2 located in a direction tilted from the normal 5n by an angle −θ, the illumination light 12 is reflected at the measurement point P of the measurement surface 5s and is received by the light receiving system R1 or light receiving system R2.

Figure 3:
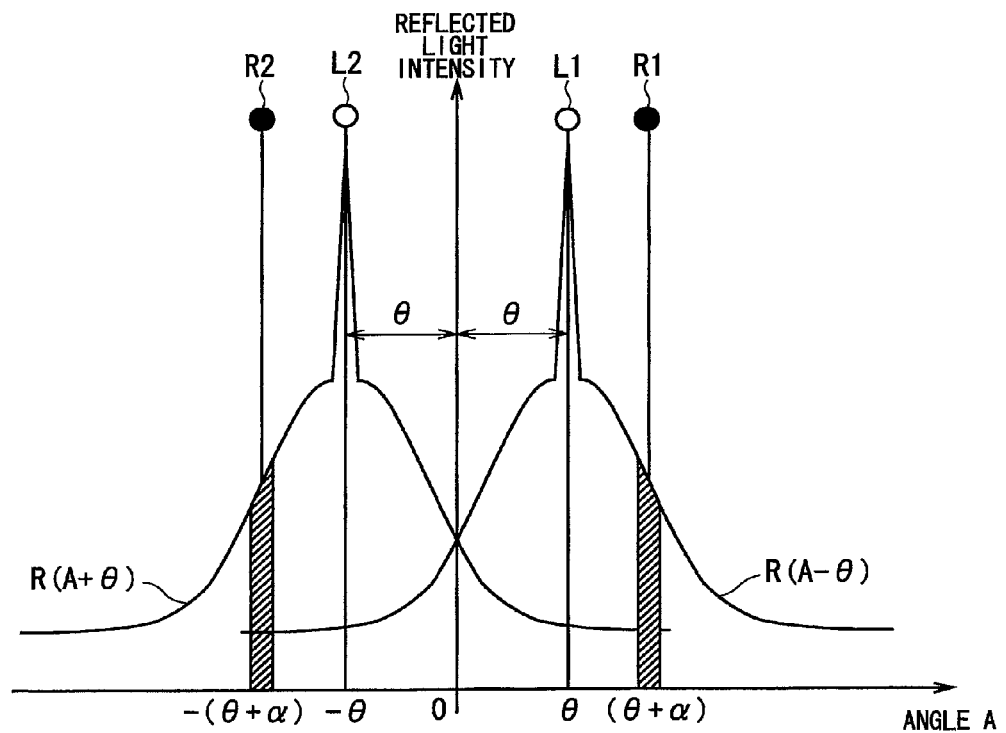
FIG. 3 is a graph showing reflected light intensities.

FIG. 3 is a graph showing reflected light intensities when the optical system and measurement surface have the positional relationship of FIG. 2. The vertical line and horizontal line represent a reflected light intensity and an angle A with respect to the normal 5n.

As shown in FIGS. 2 and 3, specularly reflected lights with respect to the illumination lights 11 and 12 from the illumination systems L1 and L2 are respectively emitted in the directions axisymmetric with the illumination lights about the normal 5n. In other words, the specularly reflected light with respect to the illumination light 11 is emitted in a direction where an angle of the location of the illumination system L2 is −θ, and the specularly reflected light with respect to the illumination light 12 is emitted in a direction where an angle of the location of the illumination system L1 is +θ. While the reflected light is generated at the positions with other angles except for the position of the center peak of the specularly reflected light, the distribution as shown in FIG. 3 is exhibited when attention is paid to the relationship between the reflected light intensity and angle A. Specifically, the components of reflection characteristics are of three types described below, and the reflection characteristics are determined by a sum of (i) to (iii).

(i) A component has a sharp peak at the angle of the specularly reflected light.

(ii) A component can be approximated by a Gaussian function that has symmetrical damping characteristics at angles of both sides in a symmetrical positional relationship about the peak angle of the specularly reflected light.

(iii) As a diffused light, a component has a peak at the normal 5n of the measurement surface 5s and can be approximated by a cosine function. A ratio of the component (ii) is large at an angle relatively close to the specularly reflected light, and a ratio of the component (iii) is large at an angle relatively remote from the specularly reflected light.

In other words, the reflected light intensity for the illumination light 11 from the illumination system L1 can be approximated to reflection characteristics R(A+θ), and the reflected light intensity for the illumination light 12 from the illumination system L2 can be approximated to reflection characteristics R(A−θ) (see FIG. 3). Accordingly, the reflected light intensity at the angle (θ+α) of the light receiving system R1 is R(+α), and the reflected light intensity at the angle −(θ+α) of the light receiving system R2 is R(−α), whereby the relationship of R(−α)=R(+α) holds in the shaded areas that indicate light amounts thereof.

Figure 4:
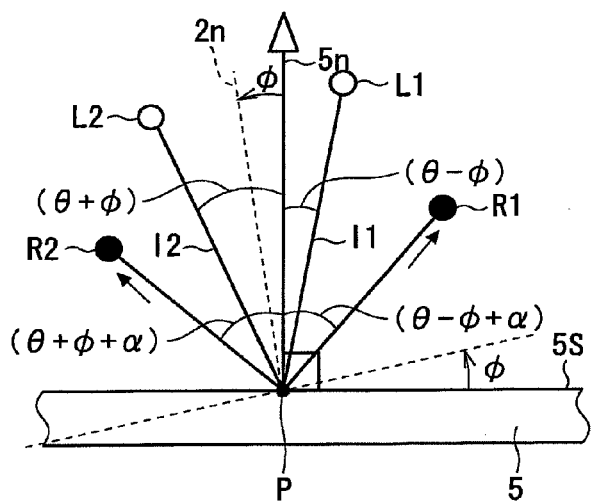
FIG. 4 is a view showing a positional relationship between the optical system and the measurement surface.

Meanwhile, FIG. 4 is a view showing the positional relationship between the optical system and measurement surface in a case where the central axis $2n$ of the measuring device body 2 is tilted in an angle $-\phi$ direction with respect to the normal $5n$ of the measurement surface $5s$. As shown in FIGS. 3 and 4, if the central axis $2n$ is tilted in the angle $-\phi$ direction with respect to the normal $5n$, the position of the illumination system L1 is tilted from the angle $+(\theta)$ to the angle $+(\theta-\phi)$ with respect to the normal $5n$, and the position of the illumination system L2 is tilted from the angle $-(\theta)$ to the angle $-(\theta+\phi)$ with respect to the normal $5n$. At the same time, the position of the light receiving system R1 is tilted from the angle $+(\theta+\alpha)$ to the angle $+(\theta+\alpha-\phi)$ with respect to the normal $5n$, and the position of the light receiving system R2 is tilted from the angle $-(\theta+\alpha)$ to the angle $-(\theta+\phi+\alpha)$ with respect to the normal $5n$.

Figure 5:
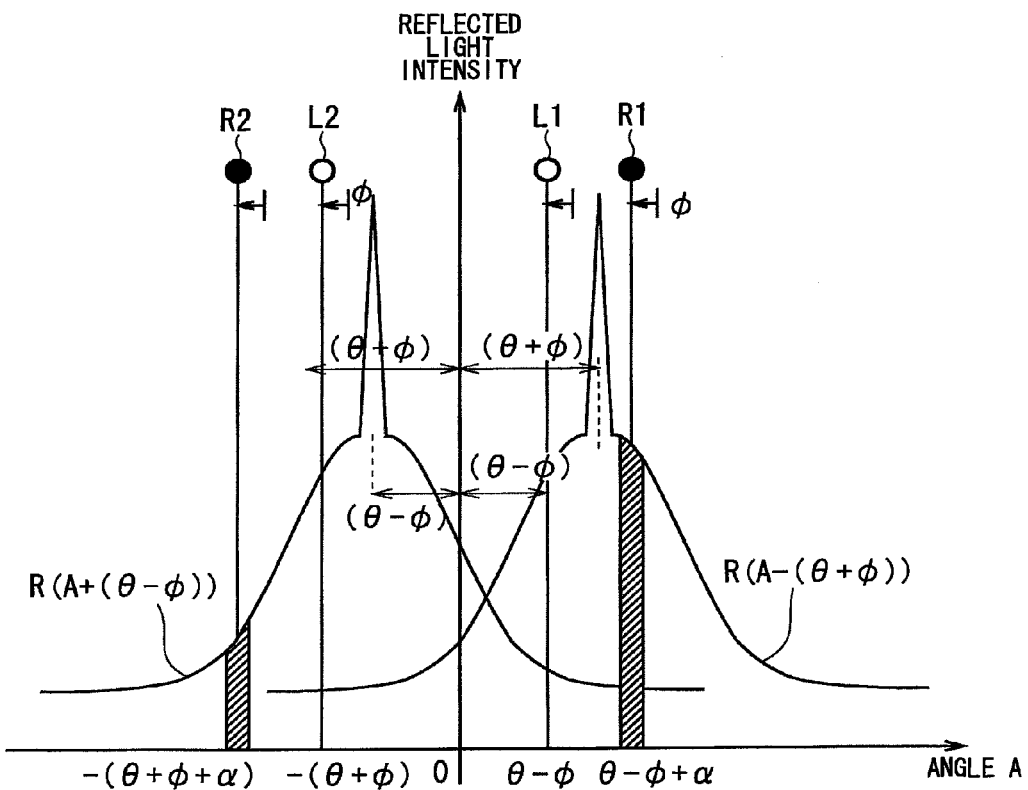
FIG. 5 is a graph showing reflected light intensities.

FIG. 5 is a graph showing reflected light intensities in a case where an illumination of light is performed while the optical system and the measurement surface have the positional relationship of FIG. 4. As shown in FIG. 5, the reflected light intensity for the illumination light 11 from the illumination system L1 can be approximated to reflection characteristics $R(A+(\theta-\phi))$, and the reflected light intensity for the illumination light 12 from the illumination system L2 can be approximated to reflection characteristics $R(A-(\theta+\phi))$. Accordingly, the reflected light intensity at the angle $+(\theta+\alpha-\phi)$ of the light receiving system R1 is $R(\alpha-2\phi)$, and the reflected light intensity at the angle $-(\theta+\phi+\alpha)$ of the light receiving system R2 is $R(-\alpha-2\phi)$, whereby the relationship of $R(\alpha-2\phi)\neq R(-\alpha-2\phi)$ holds in shaded areas that indicate light amounts thereof.

As shown in FIGS. 3 and 5, in the case where the central axis $2n$ of the measuring device body 2 is tilted in the angle $-\phi$ direction with respect to the normal $5n$ of the measurement surface $5s$, the light amount received by the light receiving system R1 is larger but the light amount received by the light receiving system R2 is smaller than those in the case where the central axis $2n$ coincides with the normal $5n$. However, if all the light amounts are taken, the light amounts are almost identical in the respective cases, where the relationship of $R(-\alpha)+R(+\alpha)=R(\alpha-2\phi)+R(-\alpha-2\phi)$ can be established approximately.

As described above, in the case where measurements are performed with the attitude in which the central axis $2n$ of the measuring device body 2 does not coincide with the normal $5n$ of the measurement surface $5s$, the color information of the measurement surface located at the measurement point P cannot be obtained accurately from the measurement information of only the light receiving system R1 (or light receiving system R2). In a case where the central axis $2n$ does not coincide with the normal $5n$, however, if the information of the reflected light is obtained independently in a symmetrical optical arrangement such as the light receiving systems R1 and R2, all the light amounts can be regarded almost equal to each other if a tilt of the measuring device is relatively small. Accordingly, the attitude error can be reduced through a correction process involving averaging.

The above is an advantage of the symmetrical arrangement mode, and the embodiments described below have both advantage of the multi-angle mode and this advantage of the symmetrical arrangement mode.

<1-3. Circumstances in Application of Symmetrical Arrangement to Multi-angle Colorimeter>

In combining the above-mentioned symmetrical arrangement mode and the multi-angle mode, unfortunately, the following problem arises: two pairs of components of the light receiving systems, such as sensors and peripheral circuit systems, are required in the multi-angle colorimeter of the multidirectional illumination and unidirectional light receiving type, and two pairs of components of the illumination systems are required in the multi-angle colorimeter of the unidirectional illumination and multidirectional light receiving type.

Under the circumstances, in the present invention, when the information of the reflected light is obtained in a symmetrical optical arrangement, the light receiving system is made common in the multi-angle colorimeter of the multidirectional illumination and unidirectional light receiving type, and the illumination system is made common in the multi-angle colorimeter of the unidirectional illumination and multidirectional light receiving type. This reduces the number of parts, which makes the multi-angle colorimeter compact, and alleviates an adverse effect due to uneven part characteristics. Accordingly, the color of the measurement surface located at the measurement point P can be measured accurately.

After the preparation described above, the specific configurations and operations of the embodiments are described below.

<2. First Embodiment>

<2-1. Functional Configuration of Multi-angle Colorimeter of Multidirectional Illumination and Unidirectional Light Receiving Type>

<2-1-1. Commonization of Optical Component (Photodetector Unit)>

Figure 6:
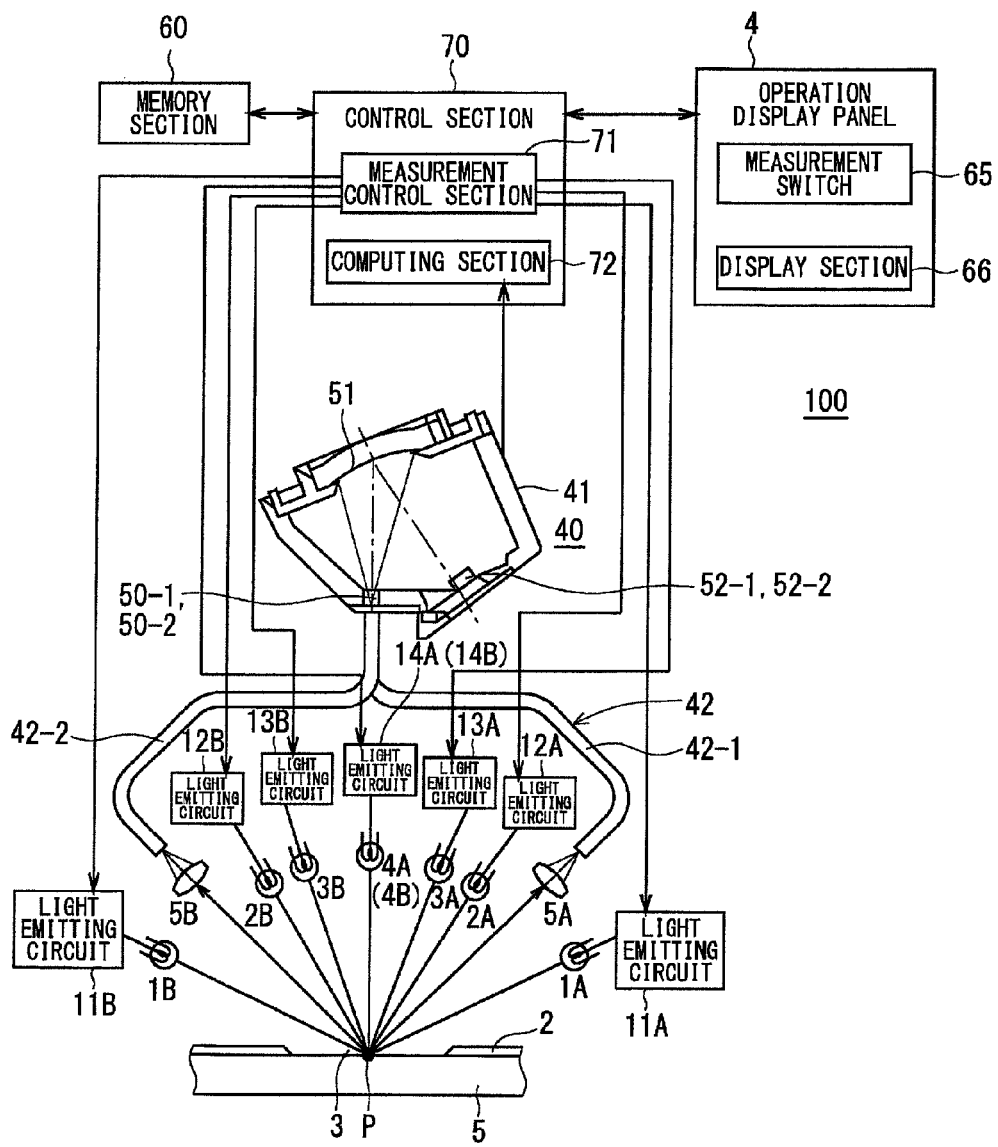
FIG. 6 is a view showing a functional configuration example of a multi-angle colorimeter according to a first embodiment.
Figure 7:
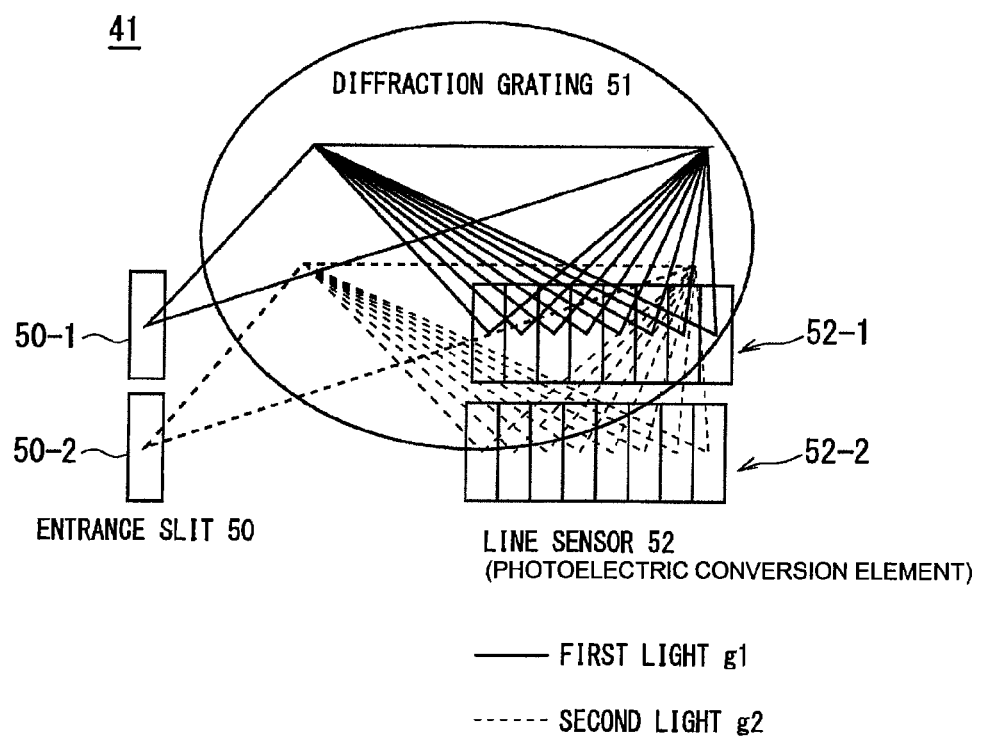
FIG. 7 is a diagram describing a photodetector unit.

FIG. 6 is a view showing a basic functional configuration of a multi-angle colorimeter 100 of the multidirectional illumination and unidirectional light receiving type according to a first embodiment of the present invention, which shows an example in which only optical fibers are arranged axisymmetrically and a photodetector unit (polychromator) is used in common. FIG. 7 is a view schematically describing an internal configuration of the photodetector unit.

As shown in FIG. 6, the multi-angle colorimeter 100 includes a photodetector section 40 and a control section 70. The photodetector section 40 includes first illumination sections 1A to 4A that are arranged on a virtual reference plane including a predetermined reference line (central axis $2n$ of the measuring device body 2) and perform light irradiation at different angles toward a predetermined measurement point P defined on the reference line, and second illumination sections 1B to 4B arranged symmetrically with the first illumination sections 1A to 4A, respectively, about the central axis $2n$ on the reference plane.

The photodetector section 40 includes a single photodetector unit 41 and an element group for introducing the light into the photodetector unit 41. An optical fiber 42 is branched into two, and the lower end surfaces of the branches serve as first and second light receiving windows 5A and 5B arranged symmetrically about the central axis $2n$. Micro lenses for efficiently focusing the reflected lights from the measurement surface on the light receiving windows 5A and 5B are arranged in front of the light receiving windows 5A and 5B. The first and second light receiving windows 5A and 5B are arranged on the reference plane, each of which facing the measurement point P. In the present application, the expression "light receiving window" does not specify a particular structure by itself but can include all of the configurations for allowing the entrance of the reflected light from the measurement surface.

The branches of the optical fiber 42 are adjacent to and parallel to each other in the upper portion thereof, upper distal ends thereof being arranged toward an entrance slit 50 of the photodetector unit 41. However, the configuration is not made so as to mix together the lights respectively from the branches of the optical fiber 42. Accordingly, the lights passing through the branches of the optical fiber 42 enter the photodetector unit 41 while being spatially separated from each other.

The photodetector unit 41 includes a photoelectric conversion element 52 that receives first and second lights g1 and g2 respectively received by the first and second light receiving windows 5A and 5B through the optical fiber 42 and an optical path component such as an optical diffraction element described below to convert spectral components of the lights g1 and g2 into electric signals.

The control section 70 includes a computing section 72 that determines detection values of the first and second lights g1 and g2 based on the electric signals and obtains the color information of the measurement surface located at the measurement point P based on the detection values. In addition, the control section 70 is provided with an operation display panel 4, a measurement switch 65, a display section 66, a memory section 60, and a measurement control section 71.

The reference plane is a plane which includes the central axis 2n and is perpendicular to the measurement surface in a case where the central axis 2n is perpendicular to the measurement surface. Hereinbelow, this plane is referred to as a "main geometry surface". A virtual plane which is orthogonal to the reference plane is referred to as a "sub-geometry surface". The multi-angle colorimeter of the present invention employs, for the tilt of the measurement surface regarding the direction parallel to the main geometry surface, the symmetrical arrangement in illumination and light receiving.

Hereinbelow, the configuration and functionality of the multi-angle colorimeter 100 are specifically described with reference to FIGS. 6 and 7.

Each of the first illumination sections 1A to 4A and second illumination sections 1B to 4B is comprised of, for example, a light source formed of a xenon flash lamp, a regulating plate that regulates a light beam from the light source, and a collimator lens (not shown). Light emitting circuits 11A to 14A and 11B to 14B that cause the light source to emit light are provided near the first illumination sections 1A to 4A and second illumination sections 1B to 4B, respectively. The first illumination sections 1A to 4A and the second illumination sections 1B to 4B are arranged to be positioned axisymmetrically about the central axis 2n, where the arrangements of 15 degrees, 45 degrees, and 110 degrees and the arrangements of 25 degrees, 45 degrees, and 75 degree are included. Those degrees are aspecular angles of optical arrangements (geometries) recommended in ASTME2194 and DIN6175-2 (2001) being two main standards in evaluation methods for metallic coating and pearl color coating. Specifically, a pair of the first illumination section 2A and second illumination section 2B, a pair of the first illumination section 3A and second illumination section 3B, and a pair of the first illumination section 4A and second illumination section 4B are each arranged to be positioned symmetrically about the central axis 2n. The illumination section 4A (4B) arranged on the central axis 2n serves as both of the first illumination section 4A and second illumination section 4B.

The light emitting circuits 11A to 14A and 11B to 14B each include, for example, a main capacitor for applying a high DC voltage of several hundred volts to an electrode of the light source, a charging circuit for charging the main capacitor, and a trigger generating circuit for applying a high AC voltage of several ten thousand volts to the trigger electrode formed of a metal wire wound in close contact with the light source. Further, the light emitting circuits 11A to 14A and 11B to 14B each include a semiconductor switch element formed of, for example, an IGBT and a drive circuit for applying a drive voltage to the semiconductor switch element.

With the semiconductor switch element being turned on and a high DC voltage being applied to electrodes on both ends of the light source by the main capacitor, a high AC voltage is momentarily applied to the trigger electrode through a trigger transformer by a trigger capacitor of the trigger generating circuit, whereby the light source is triggered. Accordingly, a DC current flows from the main capacitor, which causes light emission. Then, the semiconductor switch is turned off at a desired timing, so that light emission can be stopped.

The regulating plate is arranged such that an opening of the regulating plate coincides with a focal point of the collimator lens, and a light beam from the light source which has passed through the opening of the regulating plate is collimated by the collimator lens to turn into a parallel beam, which illuminates the measurement point P of the object to be measured 5.

The photodetector section 40 includes the first and second light receiving windows 5A and 5B that converge the parallel beams from the measurement point P of the object to be measured 5, and optical fibers 42-1 and 42-2 located at imaging positions of the first and second light receiving windows 5A and 5B. The photodetector section 40 guides the incoming light beams to the single photodetector unit 41 through the optical fibers 42-1 and 42-2. Then, the photodetector unit 41 separates the incoming light beams per wavelength and outputs the spectral data corresponding to the light intensity.

The single photodetector unit 41 includes a concave diffraction grating 51 and two line sensors (one-dimensional photoelectric conversion elements) 52-1 and 52-2, and, as shown in FIG. 7, entrance slits 50-1 and 50-2 of the photodetector unit 41 are arranged perpendicularly to the dispersion direction of the concave diffraction grating 51. The lights respectively emitted from the fibers 42-1 and 42-2 enter different areas of the concave diffraction grating 51 and are diffracted and reflected independently of each other. The resulting diffracted lights extend along the dispersion direction of the concave diffraction grating 51 and are received by two line sensors 52-1 and 52-2 arranged in the direction perpendicular to the dispersion direction. Then, the first and second lights g1 and g2 are converted into electric signals by the two line sensors 52-1 and 52-2, respectively. In other words, the concave diffraction grating 51 is shared by the first and second lights g1 and g2. In FIG. 6, the dispersion direction of the concave diffraction grating 51 is the direction along the surface of the drawing, and the direction perpendicular to the dispersion direction is the depth direction of the surface with respect to the drawing.

For this reason, the optical fiber 42 functions as a light guide section that provides the first and second lights respectively entering from the light receiving windows 5A and 5B to the photoelectric conversion elements 52-1 and 52-2 from the light receiving windows 5A and 5B in a parallel manner while those lights are spatially separated. In other words, the light guide mode of this embodiment is a mode of spatially separating lights.

The operation display panel 4 includes the measurement switch 65 for giving an instruction to start measurement, the display section 66 formed of, for example, a liquid crystal display panel for displaying measurement results, and the like.

The memory section 60 is comprised of an RAM, an EEPROM, and the like and temporarily saves the measurement results and the like. The memory section 60 also stores a control program for operating the control section 70 as follows.

The control section 70 includes an electronic circuit such as a CPU or A/D converter, includes the measurement control section 71 and the calculating section 72 as a functional block, and controls an operation of each section of the multi-angle colorimeter 100 in accordance with the control program stored in the memory section 60.

When the measurement switch 65 is operated, the measurement control section 71 causes respective light sources of the first illumination sections 1A to 4A and second illumination sections 1B to 4B to time-sequentially emit light to measure the color. Moreover, the measurement control section 71 causes the display section 66 to display calculation results obtained by the computing section 72 as the measurement results.

The computing section 72 respectively determines detection values of the first and second light g1 and g2 (spectral reflection characteristics) based on the electrical signals converted by the photodetector section 40 and obtains the color information (for example, tristimulus values) of the measurement surface located at the measurement point P based on the detection values.

In the multi-angle colorimeter 100, the illumination sections 1A to 4A and 1B to 4B are caused to time-sequentially emit light, the resulting lights reflected on the measurement surface are received through the light receiving windows 5A and 5B, and those lights are guided to the photodetector unit 41 to be diffracted and dispersed. This enables the single photodetector unit 41 to perform light dispersion and light detection for color evaluations in a multi-angle mode as well as a symmetrical arrangement mode. Among others, light dispersion is enabled by the single concave diffraction grating 51. The single photodetector unit 41 is shared by (serves as) two symmetrical measurement systems, whereby a detection error due to an individual difference in characteristics of the two photodetector units can be prevented, differently from the case where photodetector units are individually provided to two measurement systems.

FIGS. 8A to 8C show graphs showing experimental results by a device corresponding to the multi-angle colorimeter 100 of the first embodiment and a conventional device that does not have a symmetrical arrangement. FIG. 8A to FIG. 8C show the results in cases of the arrangements of 15 degrees (see FIG. 8A), 45 degrees (see FIG. 8B), and 110 degrees (see FIG. 8C), respectively, which are aspecular angles of the optical arrangements (geometries) recommended in ASTME2194 being the primary standard in the evaluation methods for metallic coating and pear color coating. The vertical line and horizontal line represent a color difference $\Delta E$ as a measurement error in the L*a*b* colorimetric system and a deviated angle between the central axis 2n and normal 5n. As shown in FIG. 8A to FIG. 8C, in a case where a symmetrical arrangement is provided (in a case where a one-side arrangement is a target for comparison, "L*a*b* correction" is added for meaning that a correction has been made by the symmetrical arrangement), a measured value error is kept smaller compared with the case in which a symmetrical arrangement is not provided (in the above-mentioned case, "without correction" is added), leading to an effect that the measurement stability is improved.

In addition to the improvement in measurement stability, the device can be downsized thanks to the photodetector unit 41 being shared.

<2-1-2. Commonization of Photodetector Unit and Switching of Optical Path (1)>

Figure 9:
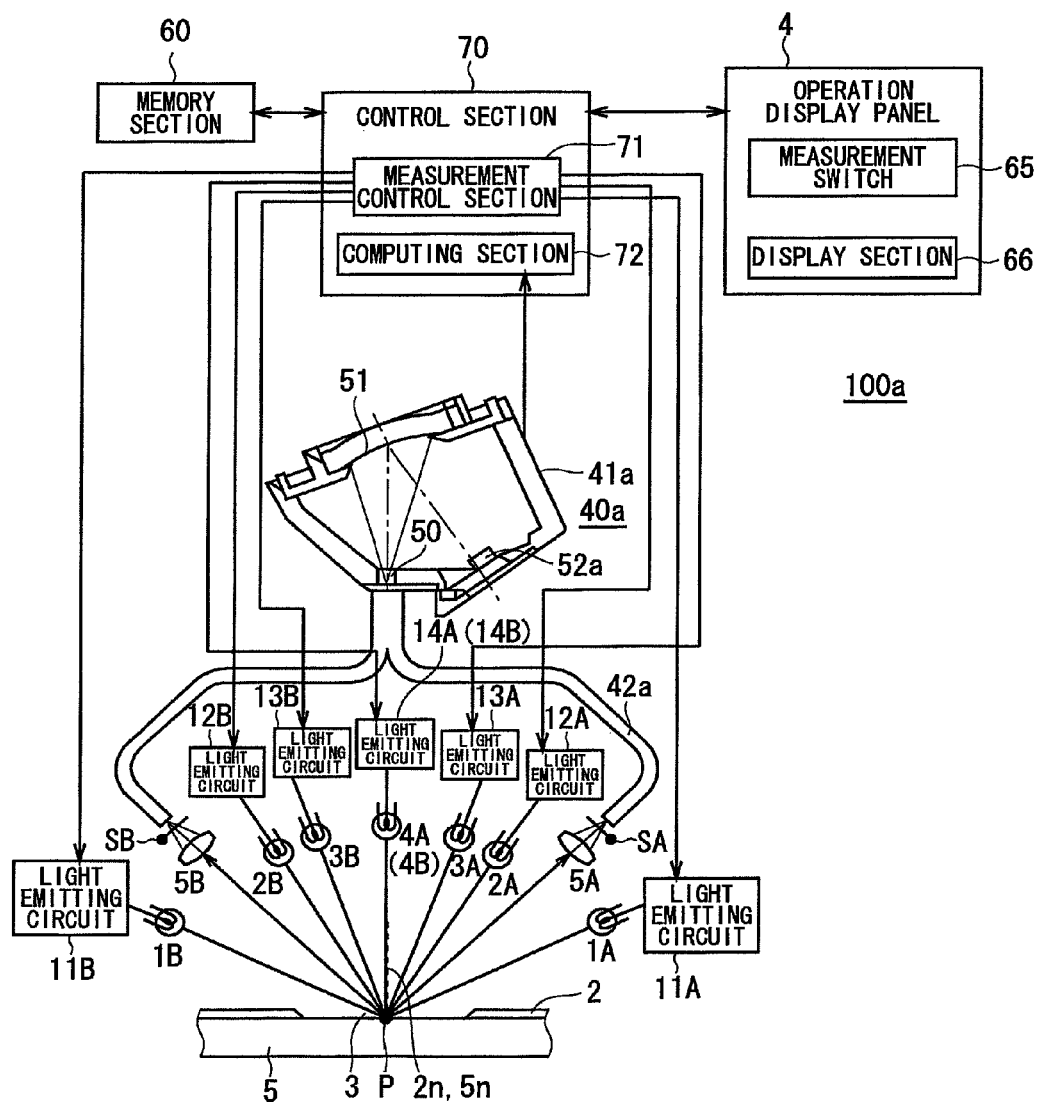
FIG. 9 is a view showing a functional configuration example of a multi-angle colorimeter according to a first modification of the first embodiment.

FIG. 9 is a view showing a basic functional configuration of a multi-angle colorimeter 100a configured to switch the optical paths of two systems on the light receiver in terms of time, as a first modification of the multi-angle colorimeter 100 in FIG. 6. The multi-angle colorimeter 100a differs from the multi-angle colorimeter 100 of FIG. 6 in that, in a photodetector section 40a, a single line sensor (photoelectric conversion element) 52a is provided and the shutters SA and SB are provided near the first and second light receiving windows 5A and 5B, respectively. There is another difference in that a bundle fiber 42a of FIG. 9 is a bundle fiber that combines lights in the entrance slit 50 while the optical fiber 42 of FIG. 6 is a fiber including two independent fibers spatially separated in the entrance slit 50. The other configuration is similar to that of the multi-angle colorimeter 100 of FIG. 6 (see FIG. 9).

Specifically, in the photodetector section 40a, as the mechanism for time-sequentially switching the measured lights received by the first and second light receiving windows 5A and 5B into the light guide system, the mechanical or optical shutters SA and SB are respectively provided, on the front surface sides of the first and second light receiving windows 5A and 5B, to the entrance opening of the bundle fiber 42a with two branches on the entrance side and one branch on the exit side that guides the light to the light receiving system. This enables on-off control corresponding to selective passing-through/interception of the lights of two systems.

The shutters SA and SB openable and closable are provided to the entrance opening of the fiber 42 in this manner, so that one shutter is closed with the other shutter open, which prevents a contribution to the measured values. This achieves the configuration in which the single line sensor 52a is provided in the photodetector unit 41a.

The shutters SA and SB and a drive section (such as small-sized motor) that selectively drives those function as a light guide section that time-divides the lights from the first and second light receiving windows 5A and 5B and selectively provides the lights to the photoelectric conversion elements.

<2-1-3. Commonization of Photodetector Unit and Switching of Optical Path (2)>

Figure 10:
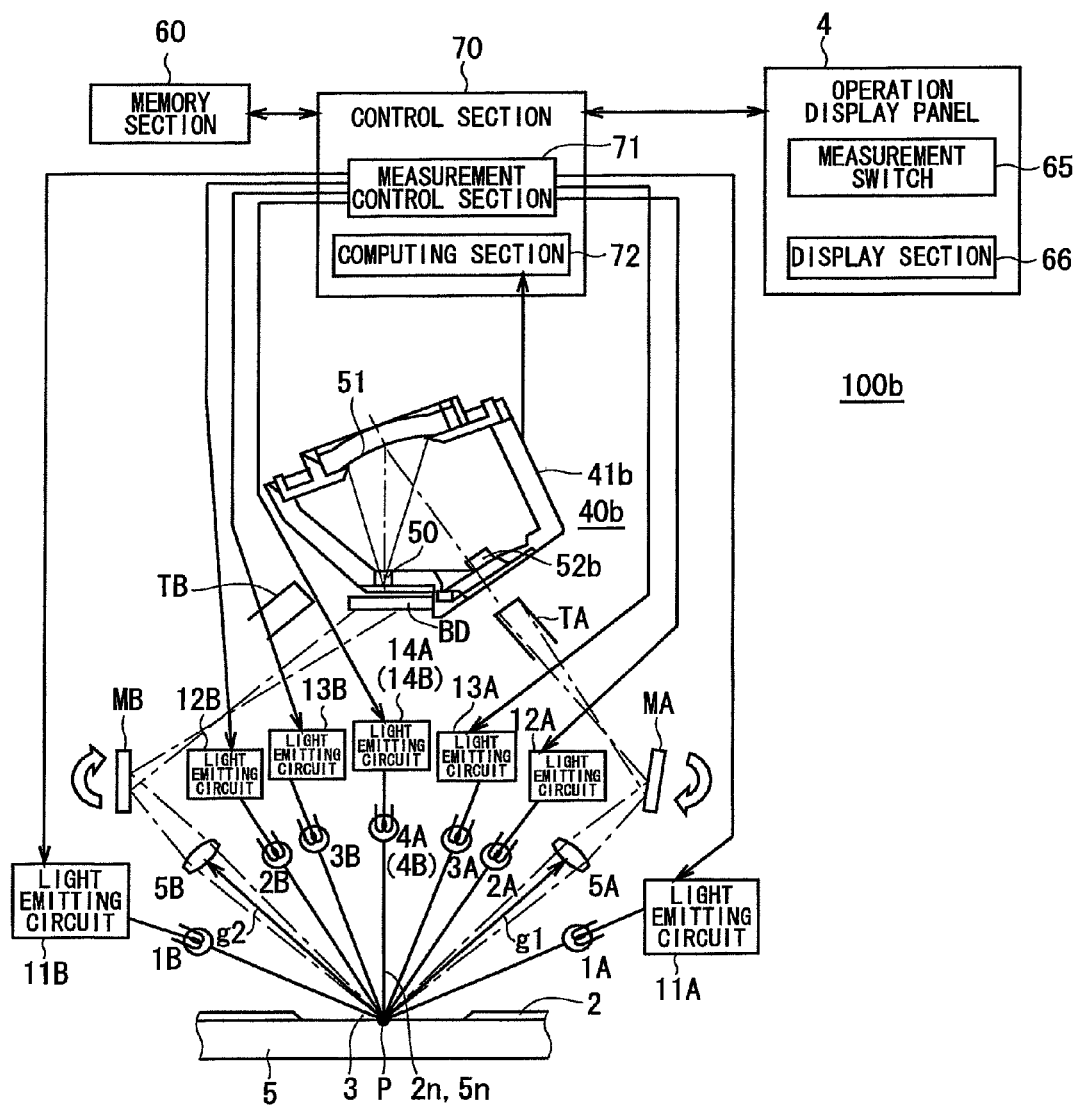
FIG. 10 is a view showing a functional configuration example of a multi-angle colorimeter according to a second modification of the first embodiment.

FIG. 10 is a view showing a basic functional configuration of a multi-angle colorimeter 100b configured to switch the optical paths of two systems on the light receiver in terms of time, as a second modification of the multi-angle colorimeter 100 of FIG. 6. The multi-angle colorimeter 100b differs from the multi-angle colorimeter 100 of FIG. 6 in that in a photodetector section 40b, a single line sensor 52b is provided in the photodetector unit 41b, a diffusing plate BD is provided at the position of the entrance slit 50 on the external side of the photodetector unit 41b, movable mirrors MA and MB are provided near the first and second light receiving windows 5A and 5B, respectively, and light traps TA and TB are provided near the photodetector unit 41. The other configuration is similar to that of the multi-angle colorimeter 100 of FIG. 6 (see FIG. 10).

Specifically, in the photodetector section 40b, the movable mirrors MA and MB are selectively rotated by, for example, a drive section such as a motor such that the movable mirrors MA and MB are selectively caused to form an angle for reflecting the light toward the photodetector unit 41b. Accordingly, the photodetector section 40b is capable of the control to time-sequentially switch the optical paths of the measured lights respectively received by the first and second light receiving windows 5A and 5B and disperse the measured lights. In other words, a first light g1 passing through the first light receiving window 5A is reflected on the movable mirror MA, and while it is intercepted by the light trap TA, the second light g2 passing through the second light receiving window 5B is reflected on the movable mirror MB and enters the entrance slit 50 through the diffusing plate BD (see FIG. 10). Conversely, a second light g2 passing through the second light receiving window 5B is reflected on the movable mirror MB, and while it is intercepted by the light trap TB, the first light g1 passing through the first light receiving window 5A is reflected on the movable mirror MA and enters the entrance slit 50 through the diffusing plate BD.

In other words, time-division light receiving is realized by the provision of the movable mirrors MA and MB, which are arranged on the optical paths of the lights respectively entering from the first and second light receiving windows 5A and 5B, and the drive section, which selectively directs the reflection directions of the lights respectively reflected on the movable mirrors MA and MB toward the photodetector unit 41b.

In this manner, the configuration is made such that the reflected lights from the measurement point P are guided to the photodetector unit 41b using the movable mirrors MA and MB, that is, such that the angles of the movable mirrors MA and MB are adjusted to allow one of the lights to enter, for example, the light trap TA or TB while the other of the lights is guided toward the photodetector unit 41b to avoid any impact on a measurement value. This realizes such a configuration that a single line sensor 52b is provided in the photodetector unit 41b.

<2-2. Control Example of Multi-angle Colorimeter>

Next, as the control example of the multi-angle colorimeter, a measurement operation is described by taking an example of the multi-angle colorimeter 100a shown in FIG. 9 among the three multi-angle colorimeters 100, 100a, and 100b as the mode of time switching. The control section 70 automatically executes this operation in accordance with the program stored in the memory section 60.

Figure 11:
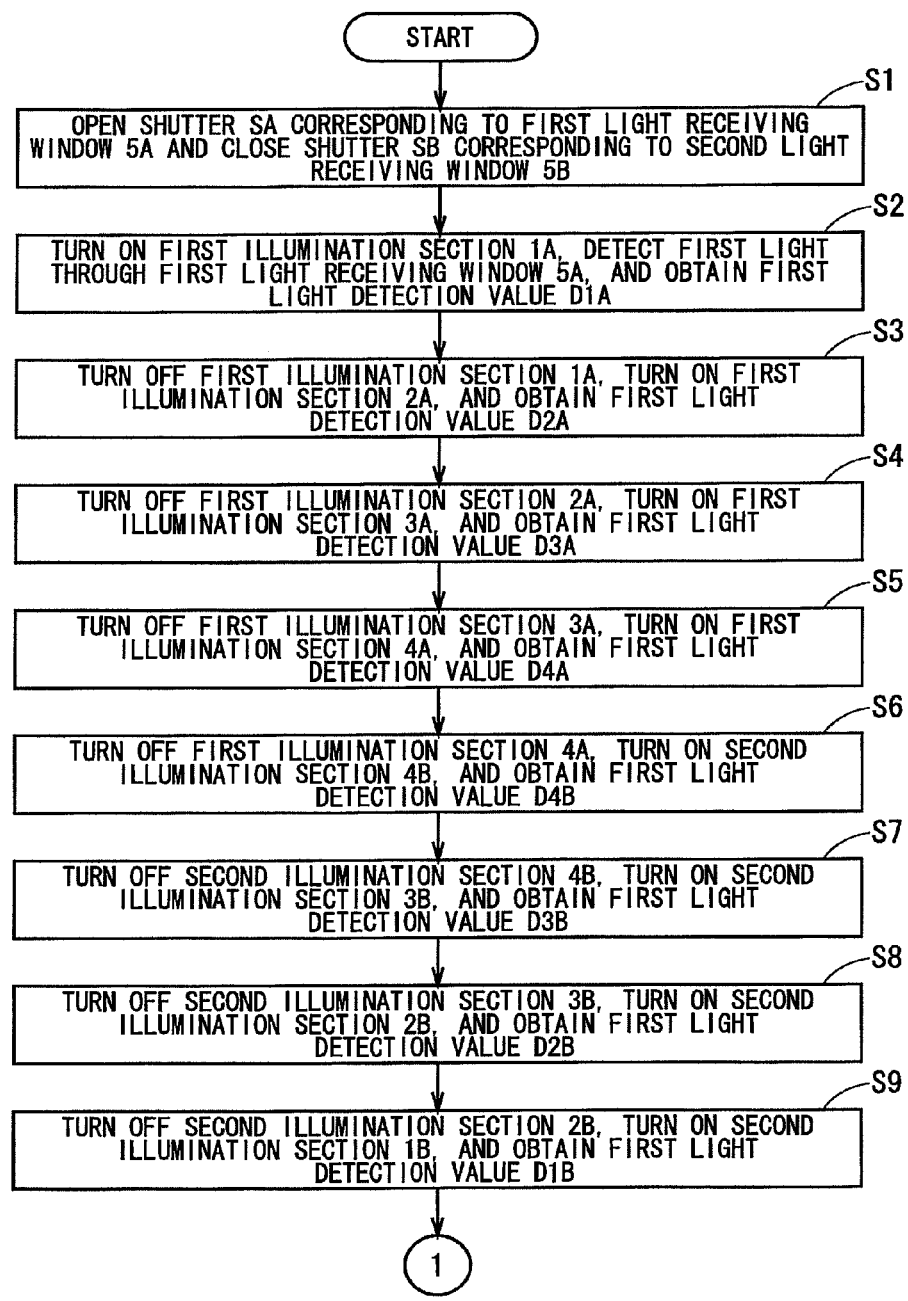
FIG. 11 is a flowchart showing an operational flow of the multi-angle colorimeter according to the first embodiment.
Figure 12:
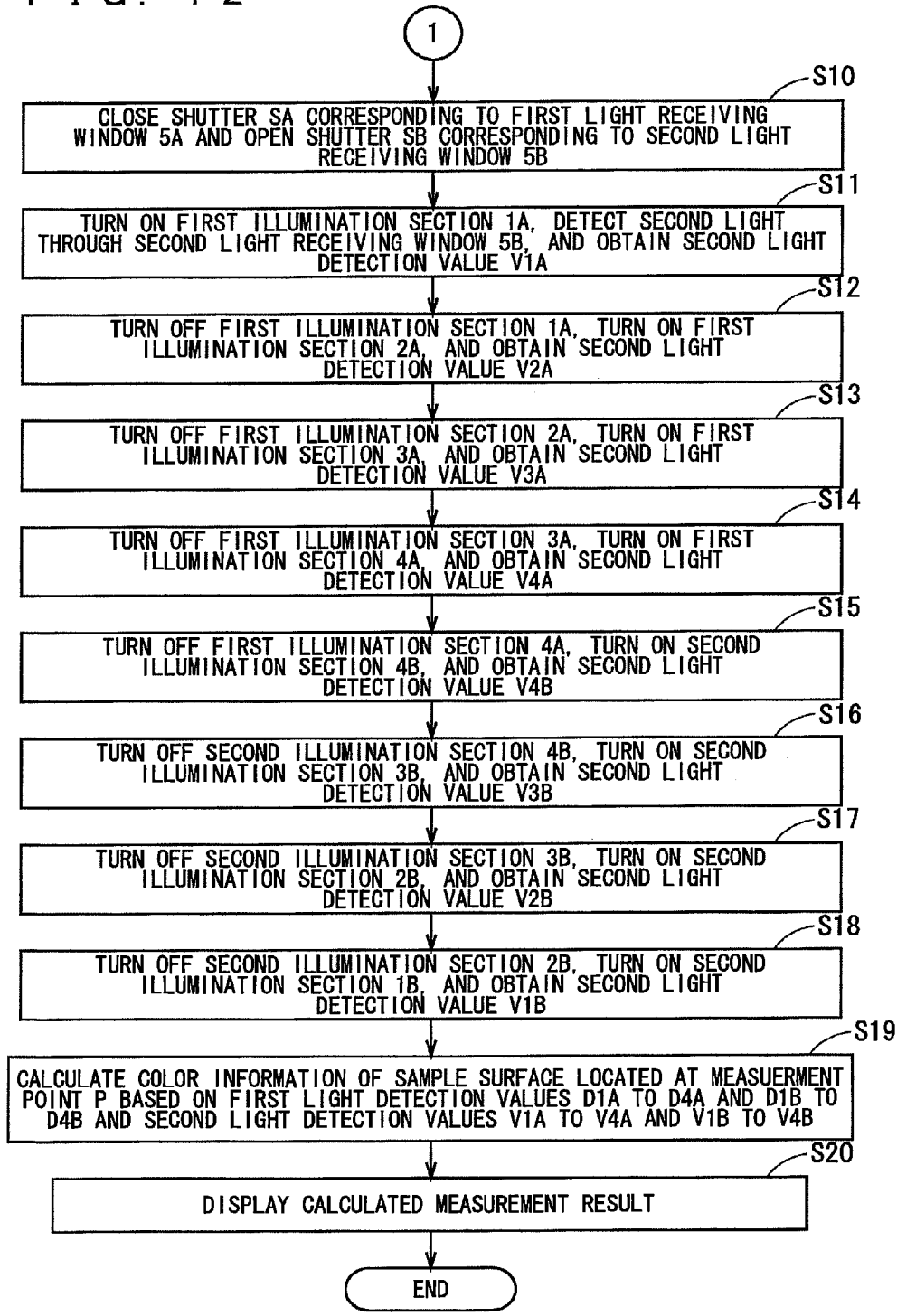
FIG. 12 is another flowchart showing the operational flow of the multi-angle colorimeter according to the first embodiment.

FIGS. 11 and 12 are flowcharts illustrating a flow of an operation realized by the multi-angle colorimeter 100a. The individual functions of the sections have been descried above, and thus, only an overall flow is described here. First, all the illuminations are turned off in starting a measurement, and then, the process moves to Step S1.

In Step S1, the measurement control section 71 causes the shutter SA corresponding to the first light receiving window 5A to open and the shutter SB corresponding to the second light receiving window 5B to close.

In Step S2, the measurement control section 71 causes the first illumination section 1A to turn on, the photodetector section 40a detects the first light g1 through the first light receiving window 5A, the computing section 72 obtains a first light detection value D1A, and the memory section 60 stores the first light detection value D1A.

In Step S3, the measurement control section 71 causes the first illumination section 1A to turn off and the first illumination section 2A to turn on, the photodetector section 40a detects the first light g1 through the first light receiving window 5A, the computing section 72 obtains a first light detection value D2A, and the memory section 60 stores the first light detection value D2A.

In Step S4, the measurement control section 71 causes the first illumination section 2A to turn off and the first illumination section 3A to turn on, the photodetector section 40a detects the first light g1 through the first light receiving window 5A, the computing section 72 obtains a first light detection value D3A, and the memory section 60 stores the first light detection value D3A.

In Step S5, the measurement control section 71 causes the first illumination section 3A to turn off and the first illumination section 4A to turn on, the photodetector section 40a detects the first light g1 through the first light receiving window 5A, the computing section 72 obtains a first light detection value D4A, and the memory section 60 stores the first light detection value D4A.

In Step S6, the measurement control section 71 causes the first illumination section 4A to turn off and the second illumination section 4B to turn on, the photodetector section 40a detects the first light g1 through the first light receiving window 5A, the computing section 72 obtains a first light detection value D4B, and the memory section 60 stores the first light detection value D4B.

In Step S7, the measurement control section 71 causes the second illumination section 4B to turn off and the second illumination section 3B to turn on, the photodetector section 40a detects the first light g1 through the first light receiving window 5A, the computing section 72 obtains a first light detection value D3B, and the memory section 60 stores the first light detection value D3B.

In Step S8, the measurement control section 71 causes the second illumination section 3B to turn off and the second illumination section 2B to turn on, the photodetector section 40a detects the first light g1 through the first light receiving window 5A, the computing section 72 obtains a first light detection value D2B, and the memory section 60 stores the first light detection value D2B.

In Step S9, the measurement control section 71 causes the second illumination section 2B to turn off and the second illumination section 1B to turn on, the photodetector section 40a detects the first light g1 through the first light receiving window 5A, the computing section 72 obtains a first light detection value D1B, and the memory section 60 stores the first light detection value D1B. After that, the second illumination section 1B is turned off.

In Step S10, the measurement control section 71 causes the shutter SA corresponding to the first light receiving window 5A to close and the shutter SB corresponding to the second light receiving window 5B to open.

In Step S11, the measurement control section 71 causes the second illumination section 1B to turn off and the first illumination section 1A to turn on, the photodetector section 40a detects the second light g2 through the second light receiving window 5B, the computing section 72 obtains a second light detection value V1A, and the memory section 60 stores the second light detection value VIA.

In Step S12, the measurement control section 71 causes the first illumination section 1A to turn off and the first illumination section 2A to turn on, the photodetector section 40a detects the second light g2 through the second light receiving window 5B, the computing section 72 obtains a second light detection value V2A, and the memory section 60 stores the second light detection value V2A.

In Step S13, the measurement control section 71 causes the first illumination section 2A to turn off and the first illumination section 3A to turn off, the photodetector section 40a detects the second light g2 through the second light receiving window 5B, the computing section 72 obtains a second light detection value V3A, and the memory section 60 stores the second light detection value V3A.

In Step S14, the measurement control section 71 causes the first illumination section 3A to turn off and the first illumination section 4A to turn on, the photodetector section 40a detects the second light g2 through the second light receiving window 5B, the computing section 72 obtains a second light detection value V4A, and the memory section 60 stores the second light detection value V4A.

In Step S15, the measurement control section 71 causes the first illumination section 4A to turn off and the second illumination section 4B to turn on, the photodetector section 40a detects the second light g2 through the second light receiving window 5B, the computing section 72 obtains a second light detection value V4B, and the memory section 60 stores the second light detection value V4B.

In Step S16, the measurement control section 71 causes the second illumination section 4B to turn off and the second illumination section 3B to turn on, the photodetector section 40a detects the second light g2 through the second light receiving window 5B, the computing section 72 obtains a second light detection value V3B, and the memory section 60 stores the second light detection value V3B.

In Step S17, the measurement control section 71 causes the second illumination section 3B to turn off and the second illumination section 2B to turn on, the photodetector section 40a detects the second light g2 through the second light receiving window 5B, the computing section 72 obtains a second light detection value V2B, and the memory section 60 stores the second light detection value V2B.

In Step S18, the measurement control section 71 causes the second illumination section 2B to turn off and the second illumination section 1B to turn off, the photodetector section 40a detects the second light g2 through the second light receiving window 5B, the computing section 72 obtains a second light detection value V1B, and the memory section 60 stores the second light detection value V1B. After that, the second illumination section 1B is turned off and the shutter SB is closed.

In Step S19, the computing section 72 calculates the color information of the measurement surface located at the measurement point P based on the first light detection values D1A to D4A and D1B to D4B and second light detection values V1A to V4A and V1B to V4B stored in the memory section 60.

Here, in Step S19, the color information of the measurement point P is obtained based on a total of 14 measured values obtained by multiplying seven illuminations of the first and second illumination sections (where the first illumination section 4A and second illumination section 4B refer to the same element) by two light receptions by the first and second light receiving windows. Specifically, based on the detection values of the first and second lights of each pair of:

first light detection value D1A in Step S2 and second light detection value V1B in Step S18,
first light detection value D2A in Step S3 and second light detection value V2B in Step S17,
first light detection value D3A in Step S4 and second light detection value V3B in Step S16,
first light detection value D4A in Step S5 and second light detection value V4B in Step S15,
first light detection value D4B in Step S6 and second light detection value V4A in Step S14,
first light detection value D3B in Step S7 and second light detection value V3A in Step S13,
first light detection value D2B in Step S8 and second light detection value V2A in Step S12, and
first light detection value D1B in Step S9 and second light detection value V1A in Step S11, the computing section 72 performs averaging individually and outputs the resultant as a measured value of each angle after correction, to thereby obtain the color information of the measurement surface located at the measurement point P. It is to be noted that regarding Steps S6 and S15, it is not required to perform the operation above because the first light detection value D4A and second light detection value V4A are obtained in Steps S5 and S14, respectively.

In Step S20, the measurement control section 71 causes the display section 66 to display, as a measurement result, the color information of the measurement surface located at the measurement point P which has been calculated by the computing section 72. Accordingly, this operational flow is finished.

As described above, the multi-angle colorimeter of the multidirectional illumination and unidirectional light receiving type has the configuration in which the photodetector unit is made common as shown in FIG. 6 and the photodetector unit is made common and the optical path is switched as shown in FIGS. 9 and 10. This enables to measure the color based on the information of the reflected light obtained with a symmetrical optical arrangement, allowing appropriate color measurement even if the central axis 2n of the measuring device body 2 is tilted from the normal 5n of the sample surface in the reference plane. In addition, the single photodetector unit 41 (41a, 41b) detects the first and second lights g1 and g2 received through the first and second light receiving windows 5A and 5B, which enables to reduce the size of the colorimeter, resulting in a reduction in cost thereof. Further, the single photodetector unit 41 (41a, 41b) is used in common, whereby internal parts thereof can be used in common. This eliminates the need to take into account an individual difference between photodetector units that is caused in a case where multiple photodetector units are used.

<3. Second Embodiment>

<3-1. Functional Configuration of Multi-angle Colorimeter of Multidirectional Illumination and Unidirectional Light Receiving Type>

Figure 13:
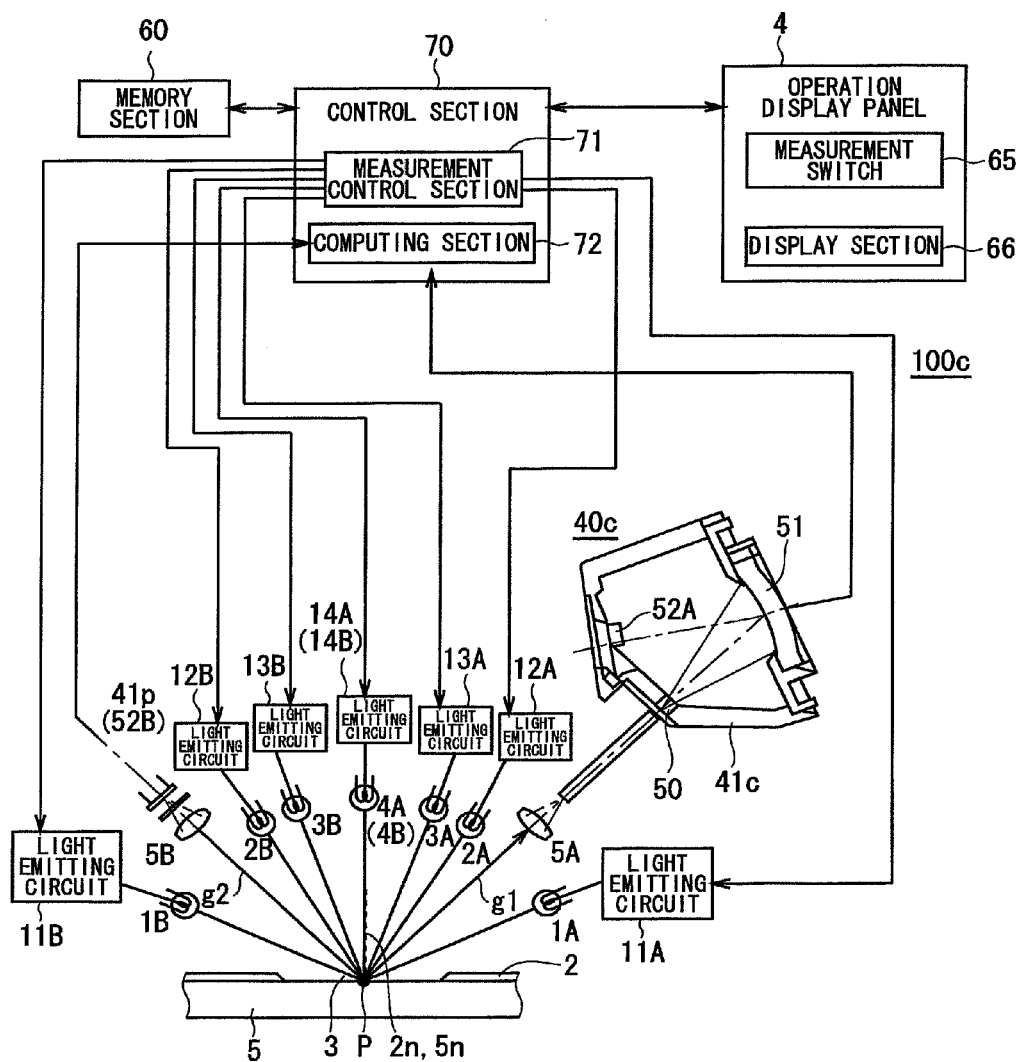
FIG. 13 is a view showing a functional configuration example of a multi-angle colorimeter according to a second embodiment.

For use in quality control in a manufacturing line, no spectral data is required and it suffices to evaluate only color values in many cases. A multi-angle colorimeter 100c described below therefore takes such a configuration as to output only color values. FIG. 13 is a view showing a basic functional configuration of the multi-angle colorimeter 100c of the multidirectional illumination and unidirectional light receiving type in a second embodiment of the present invention. This embodiment differs from the first embodiment in the employment of the configuration in which the photodetector unit is not provided in common but two photodetector units are provided, with one of the photodetector units being simplified. It is to be noted that the other configuration is similar to the device of the first embodiment, and thus, only differences therebetween are described here (see FIG. 13).

As shown in FIG. 13, the configuration of the multi-angle colorimeter 100c includes a photodetector section 40c including a first photodetector unit 41c and a second photodetector unit 41p, and the computing section 72. The first photodetector unit 41c includes a first photoelectric conversion element (linear sensor) 52A that receives a first light g1 received through the first light receiving window 5A and converts the first light g1 into an electric signal. The second photodetector unit 41p includes a second photoelectric conversion element 52B that receives a second light g2 received through the second light receiving window 5B and converts the second light g2 into an electric signal. The computing section 72 determines detection values of the first and second lights g1 and g2 based on the signals and obtains the color information of the measurement surface located at the measurement point P based on the detection values. Here, a photodetector unit having a lower wavelength resolution than that of the first photodetector unit 41c is used as the second photodetector unit 41p.

Examples of the second photodetector unit 41p having a lower wavelength resolution than that of the first photodetector unit 41c include:

a sensor configuration having spectral sensitivity with a larger bandwidth compared with a spectral sensitivity characteristic of each cell of the first photodetector unit, a sensor configuration having a peak at a single wavelength for allowing monitoring of only a specific wavelength, and a three-sensor configuration having a sensitivity corresponding to, for example, color matching functions $x(\lambda)$, $y(\lambda)$, and $z(\lambda)$.

Herein, as an example, the linear sensor 52 similar to one used in, for example, the photodetector unit 41 of FIG. 7 is used as the first photodetector unit 41c including the first photoelectric conversion element 52A, and for example, a silicon photodiode (SPD) is used as the second photodetector unit 41p including the second photoelectric conversion element 52B.

For example, by arranging the second photoelectric conversion element 52B provided with the sensitivity characteristic corresponding to a spectral luminous efficiency $V(\lambda)$, the first photoelectric conversion element 52A and the second photoelectric conversion element 52B can each obtain a value of a brightness parameter L*. An average value of those values is calculated to determine a correction factor, whereby an attitude error can be reduced.

Figure 8:
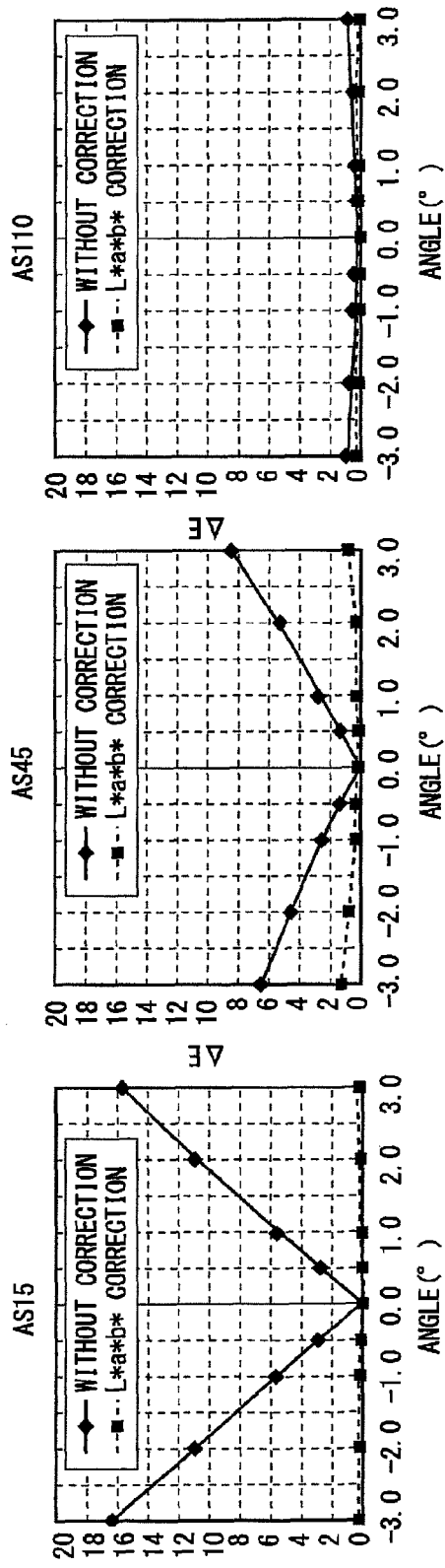
FIGS. 8A to 8C show graphs indicating measured values based on an experiment of correcting an attitude error through a symmetrical arrangement.

FIGS. 14A to 14F are graphs showing, together with the experimental results of FIGS. 8A to 8C, experimental results obtained in a case where corrections have been made to an attitude error by a symmetrical arrangement using only a brightness parameter L* indicating a brightness with the highest error sensitivity as in the second embodiment, where similarly to FIG. 8, the L*a*b* colorimetric system is taken as an example. As in FIGS. 8A to 8C, FIG. 14A to FIG. 14F respectively show the results in cases of the arrangements of 15 degrees (see FIGS. 14A and 14D), 45 degrees (see FIGS. 14B and 14D, and 110 degrees (see FIGS. 14C and 14F), which are aspecular angles of the optical arrangements (geometries) recommended in ASTME2194. As shown in FIG. 14D to FIG. 14F, in cases of L* correction only, almost similar effects to those of the cases where all the brightness L* and the chromaticities a* and b* have been corrected were obtained (see FIG. 14A to FIG. 14C).

<3-2. Control Example of Multi-angle Colorimeter>

Figure 15:
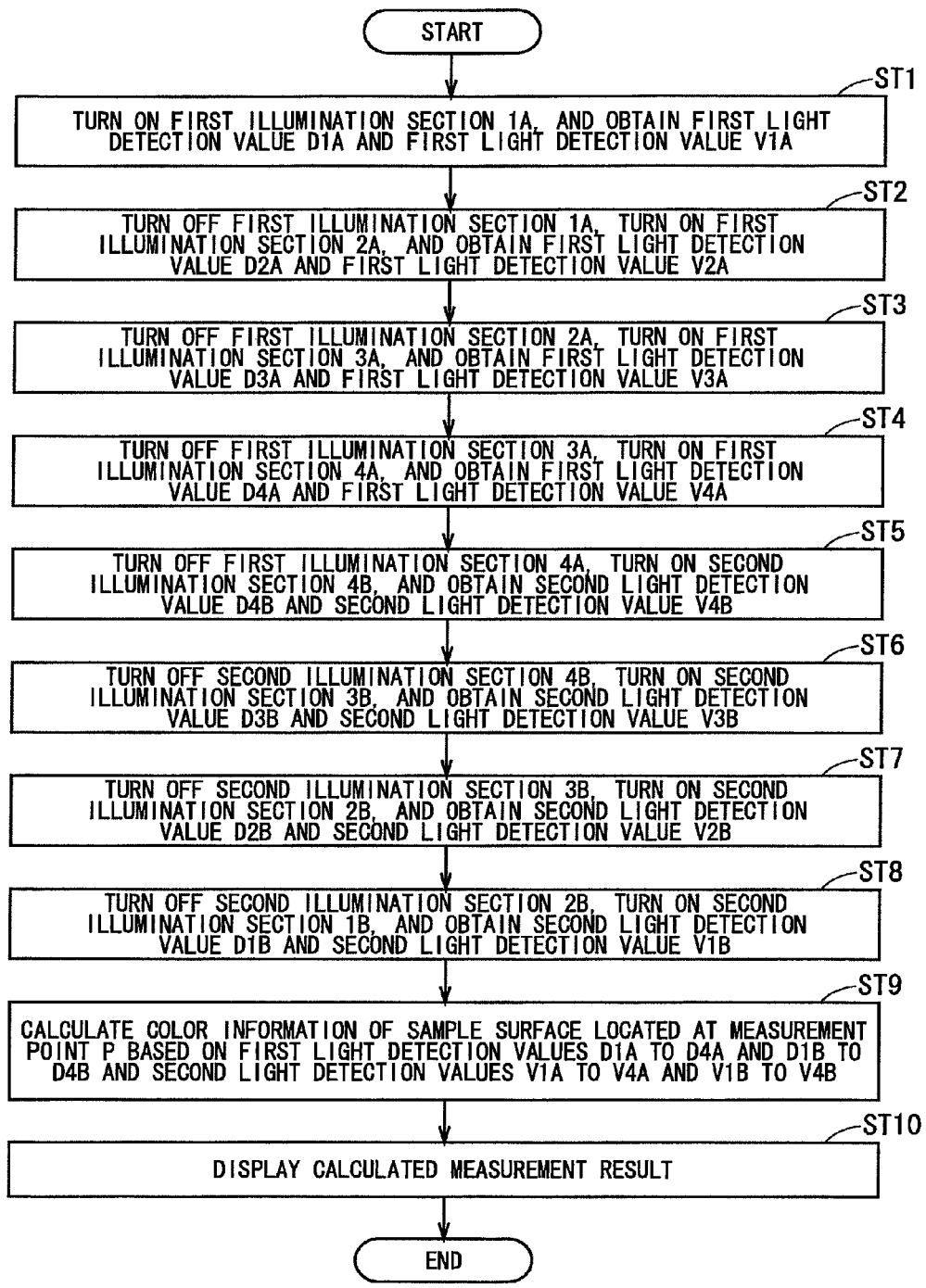
FIG. 15 is a flowchart showing an operational flow of the multi-angle colorimeter according to the second embodiment.

Next, a measurement operation of the multi-angle colorimeter 100c shown in FIG. 13 is described. FIG. 15 is a flowchart illustrating a flow of the operation realized by the multi-angle colorimeter 100c. The individual functions of the sections have been described above, and thus, only an overall flow is described here. First, all the illuminations are turned off in starting a measurement, and then, the process moves to Step ST1.

In Step ST1, the measurement control section 71 causes the first illumination section 1A to turn on, the photodetector section 40c detects a first light g1 by the first photoelectric conversion element 52A through the first light receiving window 5A, and the computing section 72 obtains a first light detection value D1A. At the same time, the photodetector section 40c detects a second light g2 by the second photoelectric conversion element 52B through the second light receiving window 5B, and the computing section 72 obtains a first light detection value V1A. Then, the memory section 60 stores those values.

In Step ST2, the measurement control section 71 causes the first illumination section 1A to turn off and the first illumination section 2A to turn on, the photodetector section 40c detects the first light g1 by the first photoelectric conversion element 52A through the first light receiving window 5A, and the computing section 72 obtains a first light detection value D2A. At the same time, the photodetector section 40c detects the second light g2 by the second photoelectric conversion element 52B through the second light receiving window 5B, and the computing section 72 obtains a first light detection value V2A. Then, the memory section 60 stores those values.

In Step ST3, the measurement control section 71 causes the first illumination section 2A to turn off and the first illumination section 3A to turn on, the photodetector section 40c detects the first light g1 by the first photoelectric conversion element 52A through the first light receiving window 5A, and the computing section 72 obtains a first light detection value D3A. At the same time, the photodetector section 40c detects the second light g2 by the second photoelectric conversion element 52B through the second light receiving window 5B, and the computing section 72 obtains a first light detection value V3A. Then, the memory section 60 stores those values.

In Step ST4, the measurement control section 71 causes the first illumination section 3A to turn off and the first illumination section 4A to turn on, the photodetector section 40c detects the first light g1 by the first photoelectric conversion element 52A through the first light receiving window 5A, and the computing section 72 obtains a first light detection value D4A. At the same time, the photodetector section 40c detects the second light g2 by the second photoelectric conversion element 52B through the second light receiving window 5B, and the computing section 72 obtains a first light detection value V4A. Then, the memory section 60 stores those values.

In Step ST5, the measurement control section 71 causes the first illumination section 4A to turn off and the second illumination section 4B to turn on, the photodetector section 40c detects the first light g1 by the first photoelectric conversion element 52A through the first light receiving window 5A, and the computing section 72 obtains a second light detection value D4B. At the same time, the photodetector section 40c detects the second light g2 by the second photoelectric conversion element 52B through the second light receiving window 5B, and the computing section 72 obtains a second light detection value V4B. Then, the memory section 60 stores those values.

In Step ST6, the measurement control section 71 causes the second illumination section 4B to turn off and the second illumination section 3B to turn on, the photodetector section 40c detects the first light g1 by the first photoelectric conversion element 52A through the first light receiving window 5A, and the computing section 72 obtains a second light detection value D3B. At the same time, the photodetector section 40c detects the second light g2 by the second photoelectric conversion element 52B through the second light receiving window 5B, and the computing section 72 obtains a second light detection value V3B. Then, the memory section 60 stores those values.

In Step ST7, the measurement control section 71 causes the second illumination section 3B to turn off and the second illumination section 2B to turn on, the photodetector section 40c detects the first light g1 by the first photoelectric conversion element 52A through the first light receiving window 5A, and the computing section 72 obtains a second light detection value D2B. At the same time, the photodetector section 40c detects the second light g2 by the second photoelectric conversion element 52B through the second light receiving window 5B, and the computing section 72 obtains a second light detection value V2B. Then, the memory section 60 stores those values.

In Step ST8, the measurement control section 71 causes the second illumination section 2B to turn off and the second illumination section 1B to turn on, the photodetector section 40c detects the first light g1 by the first photoelectric conversion element 52A through the first light receiving window 5A, and the computing section 72 obtains a second light detection value D1B. At the same time, the photodetector section 40c detects the second light g2 by the second photoelectric conversion element 52B through the second light receiving window 5B, and the computing section 72 obtains a second light detection value V1B. Then, the memory section 60 stores those values. After that, the second illumination section 1B is turned off.

In Step ST9, the computing section 72 calculates the color information of the measurement surface located at the measurement point P based on the first light detection values D1A to D4A and D1B to D4B and second light detection values V1A to V4A and V1B to V4B stored in the memory section 60.

Here, in Step ST9, the color information of the measurement point P is obtained based on a total of 14 measured values obtained by multiplying seven illuminations of the first and second illumination sections (where the first illumination section 4A and second illumination section 4B refer to the same element) by two light receptions by the first and second light receiving windows. Specifically, based on the detection values of the first and second lights of each pair of:

first light detection value D1A in Step ST1 and second light detection value V1B in Step ST8,
first light detection value D2A in Step ST2 and second light detection value V2B in Step ST7,
first light detection value D3A in Step ST3 and second light detection value V3B in Step ST6,
first light detection value D4A in Step ST4 and second light detection value V4B in Step ST5,
first light detection value D4B in Step ST5 and second light detection value V4A in Step ST4,
first light detection value D3B in Step ST6 and second light detection value V3A in Step ST3,
first light detection value D2B in Step ST7 and second light detection value V2A in Step ST2, and
first light detection value D1B in Step ST8 and second light detection value V1A in Step ST1, the computing section 72 performs averaging individually and outputs the resultant as a measured value of each angle after correction, to thereby obtain the color information of the measurement surface located at the measurement point P. It is to be noted that regarding Step ST5, it is not required to perform the operation above because the value is obtained in Step ST4.

In Step ST10, the measurement control section 71 causes the display section 66 to display, as a measurement result, the color information of the sample surface located at the measurement point P which has been calculated by the computing section 72. Accordingly, this operational flow is finished.

As described above, the multi-angle colorimeter 100c of the multidirectional illumination and unidirectional light receiving type in the second embodiment uses, as the second photodetector unit 41p, a photodetector unit having a lower wavelength resolution than that of the first photodetector unit 41c. This eliminates the need to output unnecessary spectral data, which lowers a cost, achieving a colorimeter having a compact configuration.

<4. Third Embodiment>
<4-1. Functional Configuration of Multi-angle Colorimeter of Unidirectional Illumination and Multidirectional Light Receiving Type>

Figure 16A:
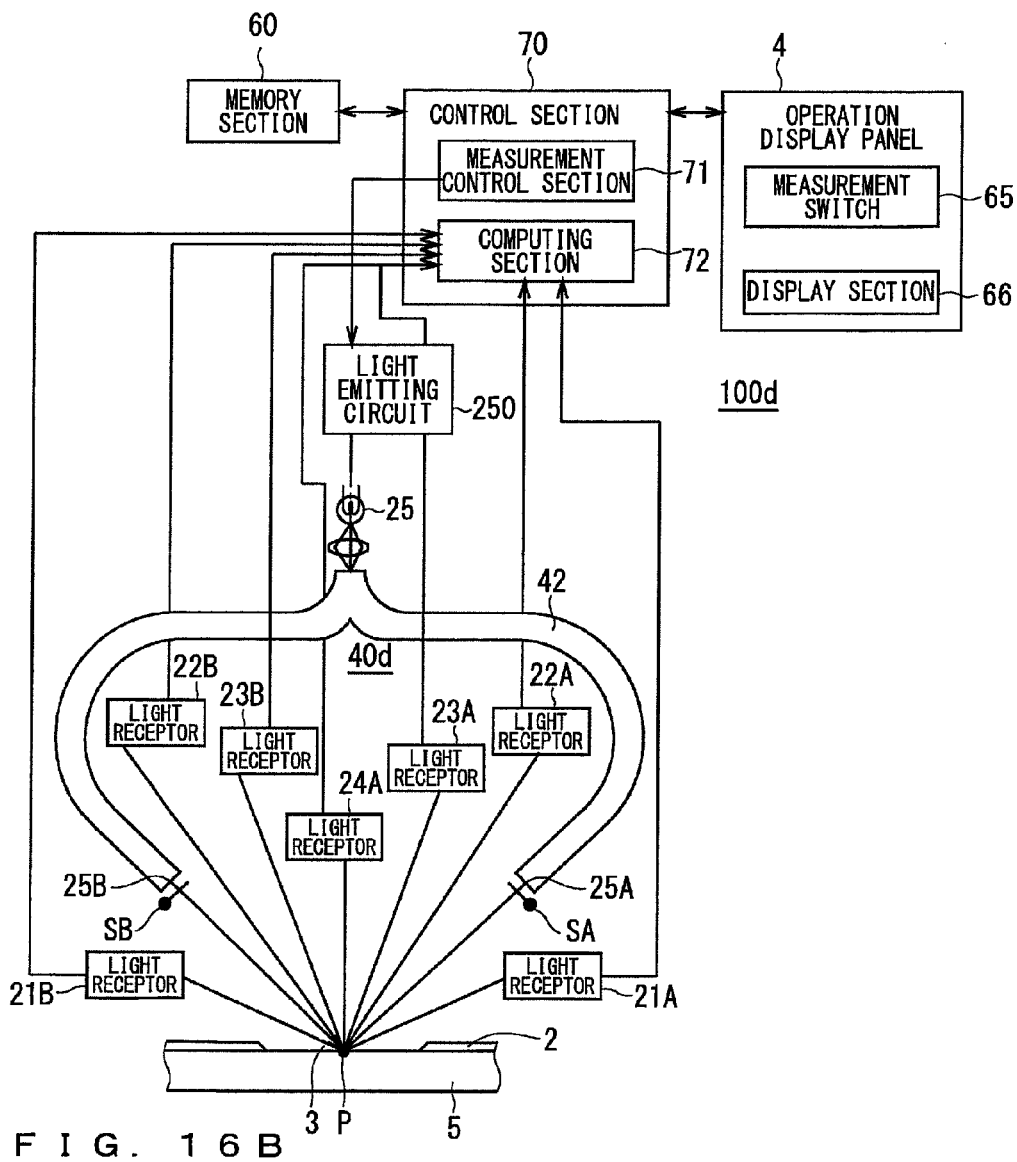
FIGS. 16A and 16B are views showing a functional configuration example of a multi-angle colorimeter according to a third embodiment.
Figure 16B:
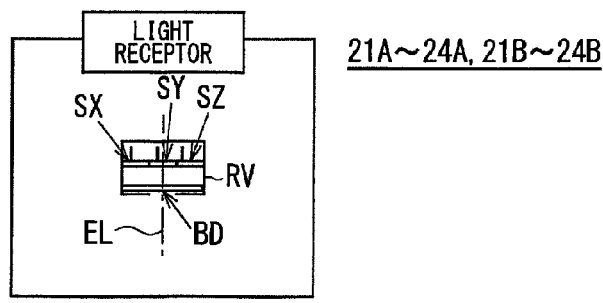

FIGS. 16A and 16B are views showing a basic functional configuration of a multi-angle colorimeter 100d of the unidirectional illumination and multidirectional light receiving type in a third embodiment of the present invention. This embodiment differs from the first embodiment in that the configuration is made such that the photodetector unit and illumination section are arranged in opposite positions. The other configuration is similar to that of the device of the first embodiment, and thus, only differences are described here (see FIGS. 16A and 16B).

As shown in FIG. 16A, the multi-angle colorimeter 100d of the unidirectional illumination and multidirectional light receiving type mainly includes:

a first illumination section 25A that is arranged on a virtual reference plane including the central axis 2n of the measuring device body 2 and performs light irradiation at a predetermined angle toward the predetermined measurement point P defined on the central axis 2n;

a second illumination section 25B that is arranged symmetrically with the first illumination section 25A about the central axis 2n on the reference plane and performs light irradiation toward the measurement point P;

a photodetector section 40d that includes multiple pairs of light receptors (photoelectric conversion elements 21A to 24A and 21B to 24B) that are arranged symmetrically about the central axis 2n on the reference plane, each pair of which facing the measurement point P; and a computing section 72 that obtains the color information of the measurement surface located at the measurement point P based on the detection values obtained from photoelectric conversion signals respectively from the multiple pairs of photoelectric conversion elements 21A to 24A and 21B to 24B. Here, the first illumination section 25A and the second illumination section 25B share the light source 25 and a light emitting circuit 250. Further, the multi-angle colorimeter 100d is provided with the optical fiber 42 as a bundle fiber with two branches on the exit side (lower-end side) and one branch on the entrance side (upper-end side). The two branches of the optical fiber 42 respectively function as a first light guide section that receives a first portion of the light from the light source 25 and guides the first portion toward the measurement point and a second light guide section that receives a second portion of the same light from the light source 25 and guides the second portion toward the measurement point. Further, the shutters SA and SB are arranged to face the lower-end sides of the fiber branches as an opening and closing section that selectively opens and closes the exits of the first portion and second portion of the light guided by the first light guide section and second light guide section. In addition, a motor (not shown) or the like that drives the shutters SA and SB is provided.

In the photodetector section 40d, the photoelectric conversion elements 21A to 24A and the photoelectric conversion elements 21B to 24B are arranged at positions symmetrical about the central axis 2n, where the arrangements of 15 degrees, 45 degrees, and 110 degrees and the arrangements of 25 degrees, 45 degrees, and 75 degrees are included. Those degrees are aspecular angles of optical arrangements (geometries) recommended in ASTME2194 and DIN6175-2 (2001) being two main standards in evaluation methods for metallic coating and pearl color coating. Specifically, pairs of the photoelectric conversion elements 21A and 21B, photoelectric conversion elements 22A and 22B, photoelectric conversion elements 23A and 23B, and photoelectric conversion elements 24A and 24B are each arranged to be positioned symmetrically about the central axis 2n. Accordingly, the same element functions as the photoelectric conversion elements 24A and 24B.

As shown in FIG. 16B, the photoelectric conversion elements 21A to 24A and 21B to 24B cause the reflected light beams from the measurement point P of the object to be measured 5 to enter a light receptor RV through the diffusing plate BD and are comprised of an X sensor SX, a Y sensor SY, and a Z sensor SZ that have spectral sensitivities respectively corresponding to color matching functions x(λ), y(λ), and z(λ). The X sensor SX, Y sensor SY, and Z sensor SZ convert incoming light beams EL (here, first and second lights g1 and g2) into electric signals corresponding to the XYZ component values in an XYZ color system.

<4-2. Control Example of Multi-angle Colorimeter>

Figure 17:
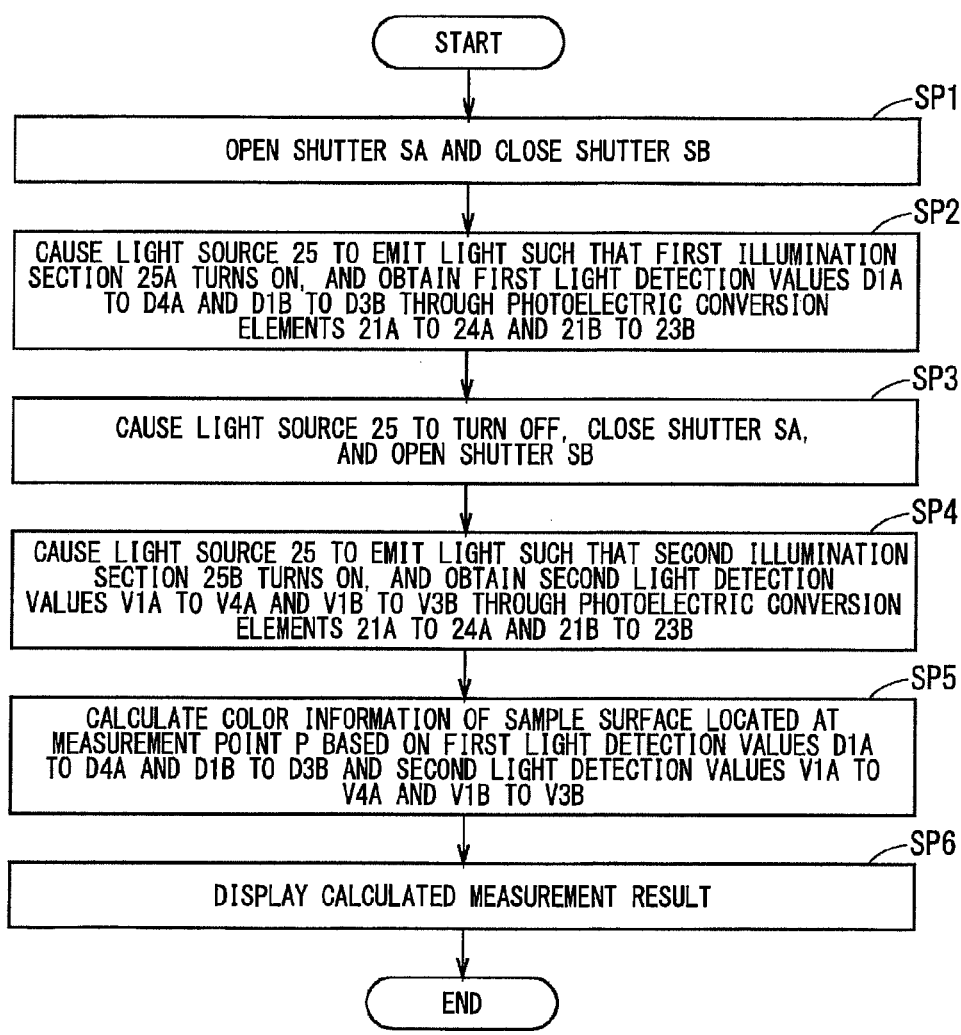
FIG. 17 is a flowchart showing an operational flow of the multi-angle colorimeter according to the third embodiment.

Next, the measurement operation of the multi-angle colorimeter 100d shown in FIGS. 16A and 16B is described. FIG. 17 is a flowchart illustrating a flow of the operation realized by the multi-angle colorimeter 100d. The individual functions of the sections have been described above, and thus, only an overall flow is described here. Hereinbelow, the photoelectric conversion element located in the direction coinciding with the central axis 2n of the measuring device body 2 is referred to as photoelectric conversion element 24A. First, the light source 25 is turned off in starting a measurement, and then, the process moves to Step SP1.

In Step SP1, the measurement control section 71 causes the shutter SA to open and the shutter SB to close.

In Step SP2, the measurement control section 71 causes the light source 25 to emit light through the light emitting circuit 250, whereby the first illumination section 25A turns on. Then, the photodetector section 40d detects a first light g1 through the photoelectric conversion elements 21A to 24A and 21B to 23B, the computing section 72 obtains first light detection values D1A to D4A and D1B to D3B, and the memory section 60 stores those values.

In Step SP3, the measurement control section 71 causes the light source 25 to turn off through the light emitting circuit 250, the shutter SA to close, and the shutter SB to open.

In Step SP4, the measurement control section 71 causes the light source 25 to emit light through the light emitting circuit 25, whereby the second illumination section 25B turns on. Then, the photodetector section 40d detects a second light g2 through the photoelectric conversion elements 21A to 24A and 21B to 23B, the computing section 72 obtains second light detection values V1A to V4A and V1B to V3B, and the memory section 60 stores those values. After that, the shutter SB is closed.

In Step SP5, the computing section 72 calculates the color information of the measurement surface located at the measurement point P based on the first light detection values D1A to D4A and D1B to D3B and second light detection values V1A to V4A and V1B to V3B stored in the memory section 60.

Here, in Step SP5, the color information of the measurement point P is obtained based on a total of 14 measured values obtained by multiplying two illuminations of the first and second illumination sections 25A and 25B by seven light receptions by the photoelectric conversion elements. Specifically, based on the detection values of the first and second lights of each pair of:

first light detection value D1A in Step SP2 and second light detection value V1B in Step SP4,
first light detection value D2A in Step SP2 and second light detection value V2B in Step SP4,
first light detection value D3A in Step SP2 and second light detection value V3B in Step SP4,
first light detection value D4A in Step SP2 and second light detection value V4A in Step SP4,
first light detection value D3B in Step SP2 and second light detection value V3A in Step SP4,
first light detection value D2B in Step SP2 and second light detection value V2A in Step SP4, and
first light detection value D1B in Step SP2 and second light detection value V1A in Step SP4, the computing section 72 performs averaging individually and outputs the resultant as a measured value of each angle after correction, to thereby obtain the color information of the measurement surface located at the measurement point P.

In Step SP6, the measurement control section 71 causes the display section 66 to display, as a measurement result, the color information of the measurement surface located at the measurement point P calculated by the computing section 72, and then, this operational flow is finished.

As described above, the multi-angle colorimeter 100d of the unidirectional illumination and multidirectional light receiving type in the third embodiment measures the color based on the information of the reflected lights obtained from a symmetrical optical arrangement, so that the color can be measured appropriately even if the central axis 2n of the measuring device body 2 is tilted from the normal 5n of the sample surface in the reference plane. In addition, the light source 25 is shared between the first illumination section 25A and the second illumination section 25B, which downsizes a colorimeter, resulting in a lower cost. Further, the light source 25 is shared, which eliminates the need to take into account an individual difference between the light sources that occurs in a case where multiple light sources are used.

<5. Fourth Embodiment>

<5-1. Functional Configuration of Multi-angle Colorimeter of Unidirectional Illumination and Multidirectional Light Receiving Type>

Figure 18:
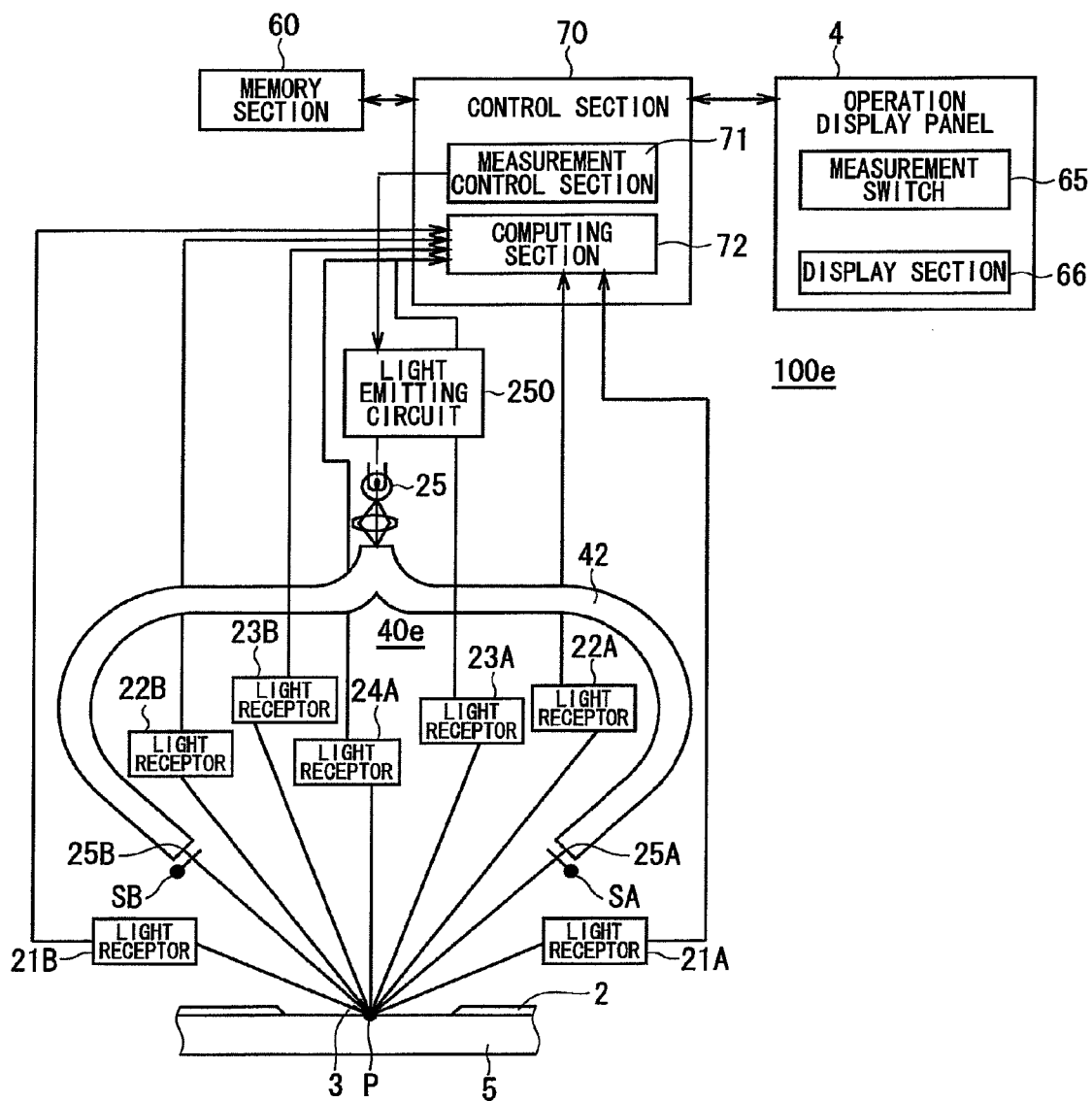
FIG. 18 is a view showing a functional configuration example of a multi-angle colorimeter according to a fourth embodiment.

FIG. 18 is a view showing a basic functional configuration of a multi-angle colorimeter 100e of the unidirectional illumination and multidirectional light receiving type in a fourth embodiment of the present invention. This embodiment differs from the third embodiment in that the configuration is made such that in the multi-angle colorimeter 100d of FIGS. 16A and 16B, the photoelectric conversion elements 21A to 24A (or 21B to 24B) among the multiple pairs that constitute pairs of the photoelectric conversion elements 21A to 24A and 21B to 24B are formed of first photoelectric conversion elements and the other photoelectric conversion elements 21B to 23B (or 21A to 23A) among the multiple pairs of photoelectric conversion elements are formed of second photoelectric conversion elements. Here, the photodetector unit including the second photoelectric conversion elements has a lower wavelength resolution than that of the photodetector unit including the first photoelectric conversion elements. The other configuration is similar to that of the device of the third embodiment, and thus, only differences are described here (see FIG. 18).

Here, as an example, the photodetector unit (polychromator) 41 of FIG. 6 is used as the photodetector unit including the first photoelectric conversion elements and the SPD of FIG. 13 is used as the photodetector unit including the second photoelectric conversion elements.

<5-2. Control Example of Multi-angle Colorimeter>

Figure 19:
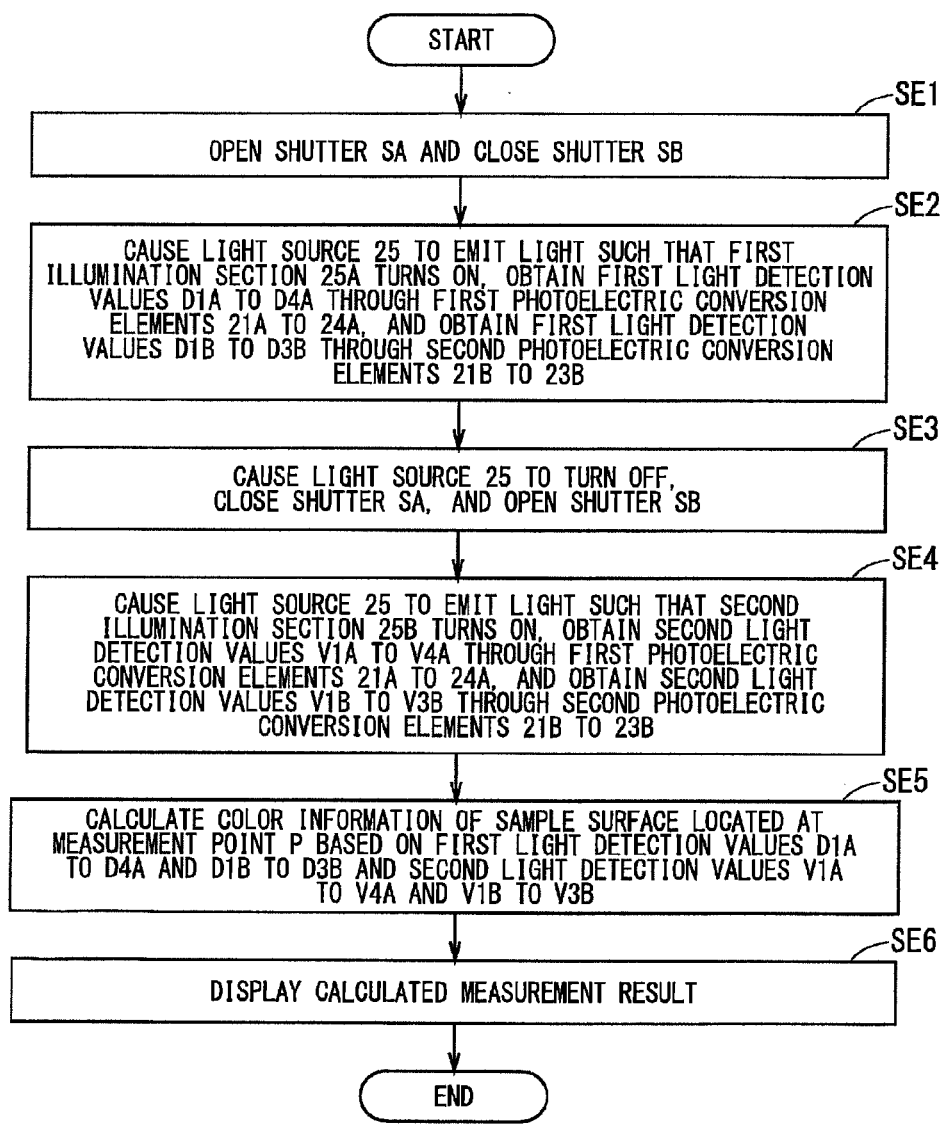
FIG. 19 is a flowchart showing an operational flow of the multi-angle colorimeter according to the fourth embodiment.

Next, the measurement operation of the multi-angle colorimeter 100e is described. FIG. 19 is a flowchart illustrating a flow of the operation realized by the multi-angle colorimeter 100e. The individual functions of the sections have been described above, and thus, only an overall flow is described here. First, all the illuminations are turned off in starting a measurement, and then, the process moves to Step SE1.

In Step SE1, the measurement control section 71 causes the shutter SA to open and the shutter SB to close.

In Step SE2, the measurement control section 71 causes the light source 25 to emit light through the light emitting circuit 250, whereby the first illumination section 25A turns on. Then, the photodetector section 40e detects a first light g1 through the first photoelectric conversion elements 21A to 24A, the computing section 72 obtains first light detection values D1A to D4A. At the same time, the photodetector section 40e detects the first light g1 through the photoelectric conversion elements 21B to 23B, and the computing section 72 obtains first light detection values D1B to D3B. Then, the memory section 60 stores those values.

In Step SE3, the measurement control section 71 causes the light source 25 to turn off through the light emitting circuit 250, the shutter SA to close, and the shutter SB to open.

In Step SE4, the measurement control section 71 causes the light source 25 to emit light through the light emitting circuit 250, whereby the second illumination section 25B turns on. Then, the photodetector section 40e detects a second light g2 through the first photoelectric conversion elements 21A to 24A, and the computing section 72 obtains second light detection values V1A to V4A. At the same time, the photodetector section 40e detects the second light g2 through the second photoelectric conversion elements 21B to 23B, and the computing section 72 obtains second light detection values V1B to V3B. Then, the memory section 60 stores those values. After that, the light source 25 is turned off and the shutter SB is closed.

In Step SE5, the computing section 72 calculates the color information of the measurement surface located at the measurement point P based on the first light detection values D1A to D4A and D1B to D3B and second light detection values V1A to V4A and V1B to V3B stored in the memory section 60.

Here, in Step SE5, the color information of the measurement point P is obtained based on a total of 14 measured values obtained by multiplying two illuminations of the first and second illumination sections 25A and 25B by seven received lights of the first photoelectric conversion elements and second photoelectric conversion elements. Specifically, based on the detection values of the first and second lights of each pair of:

first light detection value D1A in Step SE2 and second light detection value V1B in Step SE4,
first light detection value D2A in Step SE2 and second light detection value V2B in Step SE4,
first light detection value D3A in Step SE2 and second light detection value V3B in Step SE4,
first light detection value D4A in Step SE2 and second light detection value V4A in Step SE4,
first light detection value D3B in Step SE2 and second light detection value V3A in Step SE4,
first light detection value D2B in Step SE2 and second light detection value V2A in Step SE4, and
first light detection value D1B in Step SE2 and second light detection value V1A in Step SE4, the computing section 72 performs averaging individually and outputs the resultant as a measured value of each angle after correction, to thereby obtain the color information of the measurement surface located at the measurement point P.

In Step SE6, the measurement control section 71 causes the display section 66 to display, as a measurement result, the color information of the measurement surface located at the measurement point P calculated by the computing section 72, and then, this operational flow is finished.

As described above, the multi-angle colorimeter 100e uses, as the photodetector unit including the second photoelectric conversion elements 21B to 23B, a photodetector unit having a lower wavelength resolution than that of the photodetector unit including the first photoelectric conversion elements 21A to 24A. This eliminates the need to output unnecessary spectral data, which lowers a cost, realizing a colorimeter having a compact configuration.

<6. Modifications>

While the embodiments of the present invention have been described above, the present invention is not limited to the embodiments above and various modifications can be made.

While the second embodiment has described the case of the spectral luminous efficiency V(λ) as photosensitivity characteristics, other photosensitivity characteristics may be used. For example, using a bandpass filter having a sharp peak at a specific wavelength, only an output having a certain single wavelength may be monitored by the second photoelectric conversion element 52B, and a measured value may be corrected by the output.

The photodetector unit positioned in the direction coinciding with the central axis 2n of the measuring device body 2 is the photodetector unit including a first photoelectric conversion element 24A in the fourth embodiment, which may be used as the photodetector unit including the second photoelectric conversion element having a lower wavelength resolution than that of the photodetector unit including the first photoelectric conversion element.

One configuration of the multi-angle colorimeter described above includes (a) multiple first illumination sections that are arranged on a virtual reference plane including a predetermined reference line and perform light irradiation at different angles toward a predetermined measurement point defined on the reference line, (b) multiple second illumination sections that are respectively arranged symmetrically with the multiple first illumination sections about the reference line on the reference plane and perform light irradiation toward the predetermined measurement point, (c) a photodetector section including: first and second light receiving windows arranged on the reference plane, face the measurement point, and are arranged symmetrically about the reference line; and a single photodetector unit including a photoelectric conversion element that receives first and second lights respectively received through the first and second light receiving windows and converts the received lights into electric signals, and (d) a computing section that determines detection values of the first and second lights based on the signals and obtains color information of a measurement surface located at the measurement point based on the detection values.

The photodetector unit includes a single light dispersing element and first and second photoelectric conversion elements, and the multi-angle colorimeter further includes a light guide section that spatially separates the first and second lights and provides the first and second lights to the first and second photoelectric conversion elements from the first and second light receiving windows, respectively, through the light dispersing element.

Another configuration of the multi-angle colorimeter includes a light guide section that time-divides the first and second lights and provides the first and second lights to the photoelectric conversion element. The light guide section includes first and second light guide elements in which the first and second light receiving windows are respectively defined at one ends thereof, and an opening and closing section that selectively opens and closes optical paths of the first and second lights toward the first and second light receiving windows. Alternatively, the light guide section includes an optical path switching section that selectively provides the first and second lights entering through the first and second light receiving windows to the photodetector unit. The optical path switching section includes first and second mirrors arranged on optical paths from the first and second light receiving windows, respectively, and a drive section that selectively directs reflection directions of the first and second lights from the first and second mirrors toward the photodetector unit.

Another configuration of the multi-angle colorimeter described above includes (a) multiple first illumination sections that are arranged on a virtual reference plane including a predetermined reference line and perform light irradiation at different angles toward a predetermined measurement point defined on the reference line, (b) multiple second illumination sections that are respectively arranged symmetrically with the multiple first illumination sections about the reference line on the reference plane and perform light irradiation toward the predetermined measurement point, (c) a photodetector section including: first and second light receiving windows arranged on the reference plane, face the measurement point, and are arranged symmetrically about the reference line; a first photodetector unit including a first photoelectric conversion element that receives a first light received through the first light receiving window and converts the first light into an electric signal; and a second photodetector unit including a second photoelectric conversion element that receives a second light received through the second light receiving window and converts the second light into an electric signal, and (d) a computing section that determines detection values of the first and second lights based on the signals and obtains color information of a measurement surface located at the measurement point based on the detection values, wherein a photodetector unit having a lower wavelength resolution than that of the first photodetector unit is used as the second photodetector unit.

Still another configuration of the multi-angle colorimeter described above includes (a) a first illumination section that is arranged on a virtual reference plane including a predetermined reference line and performs light irradiation at a predetermined angle toward a predetermined measurement point defined on the reference line, (b) a second illumination section that is arranged symmetrically with the first illumination section about the reference line on the reference plane and performs light irradiation toward the measurement point, (c) a photodetector section including multiple pairs of photoelectric conversion elements that are arranged symmetrically about the reference line on the reference plane, each of the multiple pairs facing the measurement point, and (d) a computing section that obtains color information of a measurement surface located at the measurement point based on detection values respectively obtained from photoelectric conversion signals of the multiple pairs of photoelectric conversion elements, wherein the first illumination section and the second illumination section share a light source.

Further, in the multi-angle colorimeter, the first illumination section includes a first light guide section that receives a first portion of a light from the light source and guides the first portion toward the measurement point, a second light guide section that receives a second portion of the light from the light source and guides the second portion toward the measurement point, and an opening and closing section that selectively opens and closes exits of the first portion and the second portion of the light guided by the first light guide section and the second light guide section. One photoelectric conversion element of each of the multiple pairs of photoelectric conversion elements is formed of a first photoelectric conversion element, the other photoelectric conversion element of each of the multiple pairs of photoelectric conversion elements is formed of a second photoelectric conversion element, and a photodetector unit including the second photoelectric conversion elements has a lower wavelength resolution than that of a photodetector unit including the first photoelectric conversion elements.

The multi-angle colorimeter described above measures the color based on the information of the reflected lights achieved from a symmetrical optical arrangement, which enables to appropriately measure the color even if the reference line is tilted from the normal of the sample surface in the reference plane.

A single photodetector unit detects the first and second lights received through the first and second light receiving windows, which reduces the size of a colorimeter, resulting in a lower cost thereof. In addition, a single photodetector unit is used in common, whereby internal parts thereof can be used in common. This eliminates the need to take into account an individual difference between photodetector units that occurs in a case where multiple photodetector units are used.

A photodetector unit having a lower wavelength resolution than that of a first photodetector unit is used as a second photodetector unit, which lowers cost, realizing a colorimeter having a compact configuration.

Alternatively, the color is measured based on the information of the reflected lights obtained from a symmetrical optical arrangement, which enables to appropriately measure the color even if the reference line is tilted from the normal of the sample surface in a reference plane. Further, a light source is shared between the first illumination section and second illumination section, which lowers the size of a colorimeter, resulting in a lower cost thereof. Further, the light source is used in common, which eliminates the need to take into account an individual difference between light sources that occurs in a case where multiple light sources are used.

Alternatively, a photodetector unit having a lower wavelength resolution than that of a photodetector unit including first photoelectric conversion elements is used as a photodetector unit including second photoelectric conversion elements, which lowers a cost, realizing a colorimeter having a compact configuration.

DESCRIPTION OF REFERENCES

100, 100a to 100e multi-angle colorimeter
2 measuring device body
2n central axis
3 measurement opening
5 object to be measured
5n normal
1A to 4A, 25A first illumination section
1B to 4B, 25B second illumination section
40, 40A to 40E photodetector section
60 memory section
70 control section
71 measurement control section
72 computing section

The invention claimed is:

1. A multi-angle colorimeter comprising:
(a) multiple illumination sections that are respectively arranged on a virtual reference plane including a predetermined reference line and perform light irradiation through a measurement opening at different angles toward a predetermined measurement point defined on said reference line, wherein said predetermined reference line is a normal of said measurement opening, and wherein said illumination sections include an illumination section arranged on said reference line and at least a pair of illumination sections arranged symmetrically about said reference line;

(b) a photodetector section including:
- light receiving windows respectively arranged on said reference plane facing said measurement point, and
- a photodetector unit including a photoelectric conversion element that receives light respectively received through said light receiving windows and converts the received light into an electric signal; and (c) a computing section that determines detection values of said received light based on said electric signal and obtains color information of a measurement surface located at said measurement point based on said detection values.

2. A multi-angle colorimeter comprising:

(a) one or more illumination sections that are respectively arranged on a virtual reference plane including a predetermined reference line and perform light irradiation through a measurement opening toward a predetermined measurement point defined on said reference line, wherein said predetermined reference line is a normal of said measurement opening, (b) a photodetector section including:
- one or more light receiving windows respectively arranged on said reference plane, facing said measurement point, and
- a photodetector unit including a photoelectric conversion element that receives light respectively received through said one or more light receiving windows and converts the received light into an electric signal; and (c) a computing section that determines detection values of said received light based on said electric signal and obtains color information of a measurement surface located at said measurement point based on said detection values, wherein said one or more illumination sections include multiple illumination sections that are arranged at different angles with respect to said measurement point on said reference plane, and said multiple illumination sections include an illumination section arranged on said reference line and at least a pair of illumination sections arranged symmetrically about said reference line.

3. A multi-angle colorimeter comprising:

(a) one or more illumination sections that are respectively arranged on a virtual reference plane including a predetermined reference line and perform light irradiation through a measurement opening toward a predetermined measurement point defined on said reference line, wherein said predetermined reference line is a normal of said measurement opening, (b) a photodetector section including:
- one or more light receiving windows respectively arranged on said reference plane, facing said measurement point, and
- a photodetector unit including a photoelectric conversion element that receives light respectively received through said one or more light receiving windows and converts the received light into an electric signal; and (c) a computing section that determines detection values of said received light based on said electric signal and obtains color information of a measurement surface located at said measurement point based on said detection values, wherein said one or more receiving windows include multiple receiving windows that are arranged at different angles with respect to said measurement point on said reference plane, and said multiple receiving windows include a receiving window arranged on said reference line and at least a pair of receiving windows arranged symmetrically about said reference line.

4. The multi-angle colorimeter of claim 3, wherein said one or more illumination sections include multiple illumination sections that are arranged at different angles with respect to said measurement point on said reference plane, and said multiple illumination sections include an illumination section arranged on said reference line and at least a pair of illumination sections arranged symmetrically about said reference line.

* * * * *